US008592179B2

(12) United States Patent
Schraeml et al.

(10) Patent No.: US 8,592,179 B2
(45) Date of Patent: Nov. 26, 2013

(54) ARTIFICIAL BINDING PROTEINS BASED ON A MODIFIED ALPHA HELICAL REGION OF UBIQUITIN

(75) Inventors: Michael Schraeml, Penzberg (DE); Erik Fiedler, Halle (DE)

(73) Assignee: Scil Proteins GmbH, Halle/Saale (DE)

( * ) Notice: Subject to any disclaimer, the term of this patent is extended or adjusted under 35 U.S.C. 154(b) by 439 days.

(21) Appl. No.: 12/514,550

(22) PCT Filed: Nov. 15, 2007

(86) PCT No.: PCT/EP2007/062375
§ 371 (c)(1),
(2), (4) Date: Jan. 19, 2010

(87) PCT Pub. No.: WO2008/059011
PCT Pub. Date: May 22, 2008

(65) Prior Publication Data
US 2010/0130720 A1    May 27, 2010

(30) Foreign Application Priority Data

Nov. 15, 2006 (EP) .................................. 06124137

(51) Int. Cl.
C07K 14/435 (2006.01)
(52) U.S. Cl.
USPC ......................................... 435/69.1; 530/324
(58) Field of Classification Search
USPC ....................................................... 435/69.1
See application file for complete search history.

(56) References Cited

U.S. PATENT DOCUMENTS

| 4,873,192 | A | 10/1989 | Kunkel |
| 5,789,166 | A | 8/1998 | Bauer et al. |
| 5,958,684 | A | 9/1999 | Van Leeuwen et al. |
| 6,569,677 | B1 | 5/2003 | Legrand et al. |
| 6,673,901 | B2 | 1/2004 | Koide |
| 6,799,121 | B2 | 9/2004 | Chu et al. |
| 7,250,297 | B1 | 7/2007 | Beste et al. |
| 7,601,803 | B1 | 10/2009 | Fiedler et al. |
| 7,838,629 | B2 | 11/2010 | Fiedler et al. |
| 2003/0073623 | A1 | 4/2003 | Drmanac et al. |
| 2004/0043386 | A1 | 3/2004 | Pray et al. |
| 2006/0058510 | A1 | 3/2006 | Skerra et al. |
| 2006/0099686 | A1* | 5/2006 | Fiedler et al. ................. 435/69.1 |
| 2007/0111287 | A1 | 5/2007 | Fiedler et al. |
| 2007/0248536 | A1 | 10/2007 | Fiedler et al. |
| 2008/0171851 | A1 | 7/2008 | Fiedler et al. |
| 2013/0011334 | A1 | 1/2013 | Steuernagel et al. |
| 2013/0097737 | A1 | 4/2013 | Kovalic et al. |

FOREIGN PATENT DOCUMENTS

| AU | 2010332932 | 6/2011 |
| AU | 2010332938 | 6/2011 |
| FR | 2 761 688 A | 10/1998 |
| WO | WO97/16556 | 5/1997 |
| WO | WO97/45544 | 12/1997 |
| WO | WO98/54312 | 12/1998 |
| WO | WO99/58570 | 11/1999 |
| WO | WO01/62298 | 8/2001 |
| WO | WO01/62800 | 8/2001 |
| WO | WO 2004/106368 | 12/2004 |
| WO | WO 2005/044845 | 5/2005 |
| WO | WO 2005/059131 | 6/2005 |
| WO | WO2006/119897 | 11/2006 |
| WO | WO2007/054120 | 5/2007 |
| WO | WO2007/115837 | 10/2007 |
| WO | WO2007/128563 | 11/2007 |
| WO | WO2008/022759 | 2/2008 |
| WO | WO2008/059011 | 5/2008 |
| WO | WO2008/096012 | 8/2008 |
| WO | WO2011/073208 | 6/2011 |
| WO | WO2011/073209 | 6/2011 |
| WO | WO2011/073214 | 6/2011 |

OTHER PUBLICATIONS

Branden et al.; Introduction to Protein Structure, Garland Publishing Inc., New York, p. 247 (1991).*
Witkowski et al.; Conversion of a beta-ketoacyl synthase to a malonyl decarboxylase by replacement of the active-site cysteine with glutamine; Biochemistry 38:11643-11650, (1999).*
Seffernick et al.; Melanine deaminase and atrazine chlorohydrolase: 98 percent identical but functionally different; J. Bacteriol. 183(8):2405-2410, (2001).*
Bofill et al., "Engineering Stabilising beta-Sheet Interactions into a Conformationally Flexible Region of the Folding Transition State of Ubiquitin," Journal of Molecular Biology, London, GB, vol. 353, No. 2, pp. 373-384 (Oct. 21, 2005), XP005086541 ISSN: 0022-2836.
Ermolenko et al., "Noncharged amino acid residues at the solvent-exposed positions in the middle and at the C terminus of the alpha-helix have the same helical propensity," Protein Science, vol. 12, No. 6, pp. 1169-1176 (Jun. 2003), XP00243791 T ISSN: 0961-8368.
International Preliminary Report on Patentability corresponding to International Application No. PCT/EP2007/062375 dated May 19, 2009.
Krantz et al., "Discerning the Structure and Energy of Multiple Transition States in Protein Folding using psi-Analysis," Journal of Molecular Biology, London, GB, vol. 337, No. 2, pp. 463-475 (Mar. 19, 2004), XP004493197 ISSN: 0022-2836.

(Continued)

Primary Examiner — Michele K Joike
Assistant Examiner — Antonio Galisteo Gonzalez
(74) Attorney, Agent, or Firm — Jenkins, Wilson, Taylor & Hunt, P.A.

(57) ABSTRACT

The present invention is directed to a method for the generation of binding proteins derived from the protein super-family of ubiquitin like proteins with modifications in their alpha helical region as well as to a protein obtainable by said method. Furthermore, the invention provides the use of a protein for the specific recognition, binding and neutralization of a predescribed target molecule, for the detection, quantitative determination, separation and/or for the isolation of a corresponding binding partner and the use of a protein of the invention, for diagnosis, prophylaxis and treatment of diseases in which the corresponding binding partner is directly or indirectly involved.

28 Claims, 12 Drawing Sheets

(56) References Cited

OTHER PUBLICATIONS

Loladze et al., "Both helical propensity and side-chain hydrophobicity at a partially exposed site in alpha-helix contribute to the thermodynamic stability of ubiquitin," Proteins, vol. 58, No. 1, pp. 1-6 (Jan. 1, 2005), XP002437914 ISSN: 1097-0134.
Yang et al., "Relationship between folding and function in a sequence-specific miniature DNA-binding protein," Biochemistry, vol. 44, No. 20, pp. 7469-7478 (May 24, 2005), XP002437916 ISSN: 0006-2960.
Yeh et al., "Ubiquitin-like proteins: new wines in new bottles," Gene, Elsevier, Amsterdam, NL, vol. 248, No. 1-2, pp. 1-14 (May 2000), XP004198791 ISSN: 0378-1119.
Abedi et al, "Green Fluorescent protein as a scaffold for intracellular presentaion of peptides," Nucleic Acids Research, vol. 26, No. 2 pp. 623-630 (1998).
Advisory Action corresponding to U.S. Appl. No. 10/030,605 dated Oct. 13, 2006.
Advisory Action corresponding to U.S. Appl. No. 12/072,959 dated May 18, 2010.
Advisory Action corresponding to U.S. Appl. No. 11/732,632 dated Jun. 30, 2010.
Baker et al., "Protein Expression Using Cotranslational Fusion and Cleavage of Ubiquitin," The Journal of Biological Chemistry. vol. 269, No. 41 pp. 25381-25386 (1994).
Beal et al., "Surface hydrophobic residues of multiubiquitin chains essential for proteolytic targeting," PNAS. vol. 93 pp. 861-866 (1996).
Beste, et al., "Small antibody-like proteins with prescribed ligand specificities derived from the lipocalin fold," PNAS. vol. 96 pp. 1898-1903 (1999).
Bird et al., "Single-Chain Antigen-Binding Proteins," Science. vol. 242 pp. 423-426 (1988).
Bolton et al., "Structure and Properties of a Dimeric N-terminal Fragment of Human Ubiquitin," Journal of Molecular Biology. vol. 314 pp. 773-787 (2001).
Brinkmann et al., "A recombinant immunotoxin containing a disulfide-stabilized Fv-fragment," PNAS. vol. 90 pp. 7538-7542 (1993).
Brinkmann et al., "Stabilization of a Recombinant Fv Fragment by Base-Loop Interconnection and VH-VL Permutation," Journal of Molecular Biology. vol. 268 pp. 107-117 (1997).
Buchberger et al., "The UBX Domain: A Widespread Ubiquitin-Like Module," Journal of Molecular Biology. vol. 307, No. 1 pp. 17-24 (2001).
Burch, T.J., and Haas, A.L., "Site-directed mutagenesis of ubiquitin. Differential roles for arginine in the interaction with ubiquitin-activating enzyme," Biochemistry. vol. 33, No. 23 pp. 7300-7308 (1994) [Abstract].
Campion et al., "Biochemical Properties of Site-Directed Mutants of Human Epidermal Growth Factor: Importance of Solvent-Exposed Hydrophobic Residues of the Amino-Terminal Domain in Receptor Binding," Biochemistry. vol. 29, No. 42 pp. 9988-9993 (1990).
Connolly, "Solvent-Accessible Surfaces of Proteins and Nucleic Acids." Science. vol. 221, No. 4612 pp. 709-713 (1983).
Daugherty et al., "Antibody affinity maturation using bacterial surface display," Protein Engineering. vol. 11, No. 9 pp. 825-832 (1998).
de Kruif et al., "Selection and Application of Human Single Chain Fv Antibody Fragments from a Semi-synthetic Phage Antibody Display Library with Designed CDR3 Regions," Journal of Molecular Biology. vol. 248 pp. 97-105 (1995).
Ebersbach et al., "Affilin-Novel Binding Molecules Based on Human (-B-Crystallin, an All (-Sheet Protein," Journal of Molecular Biology. vol. 372 pp. 172-185 (2007).
Ecker et al., "Gene Synthesis, Expression, Structures, and Functional Activities of Site-specific Mutants of Ubiquitin," The Journal of Biological Chemistry, vol. 262, No. 29 pp. 14213-14221 (1987).
European Office Action corresponding to European Patent Application No. 00 944 034.8-2401 dated Oct. 7, 2004. [not in English; P13840].

European Patent Office Examination Report corresponding to European Patent Application No. 06118519.5-2401 dated Apr. 2, 2007. [not in English].
European Search Report corresponding to European Patent Application No. EP 10181802.9-2401 dated Feb. 10, 2011.
European Search Report corresponding to European Patent Application No. 09176574.3-2401 dated Jan. 18, 2010.[need English translation—ask for translation from client in 1406/305; clt. stated not material enough to translate].
Fiedler et al., "Affilin™ Molecules: Novel Ligands for Bioseparation," Trans IChemE, Part C, Food and Bioproducts Processing. vol. 84, No. C1 pp. 3-8 (2006).
Finucane et al., "Core-Directed Protein Design. I. An Experimental Method for Selecting Stable Proteins from Combinatorial Libraries," Biochemistry. vol. 38 pp. 11604-11612 (1999).
Finucane, et al., "Core-Directed Protein Design. II. Rescue of a Multiply Mutated and Destabilized Variant of Ubiquitin." Biochemistry. vol. 38, No. 36 pp. 11613-11623 (1999).
Gebauer, M., and Skerra, A., "Engineered protein scaffolds as next-generation antibody therapeutics," Current Opinion in Chemical Biology. vol. 13 pp. 245-255 (2009).
Grabulovski et al., "A Novel, Non-immunogenic Fyn SH3-derived Binding Protein with Tumor Vascular Targeting Properties," The Journal of Biological Chemistry. vol. 282, No. 5 pp. 3196-3204 (2007).
Guo et al., "Protein tolerance to random amino acid change," PNAS. vol. 101, No. 25 pp. 9205-9210 (2004).
Hanes, J., and Pluckthun, A., "In vitro selection and evolution of functional proteins by using ribosome display," PNAS. vol. 94 pp. 4937-4942 (1997).
Hanes et al., "Picomolar affinity antibodies from a fully synthetic naive library selected and evolved by ribosome display," Nature Biotechnology. vol. 18 pp. 1287-1292 (2000).
Hanes et al., "Ribosome display efficiently selects and evolves high-affinity antibodies in vitro from immune libraries," PNAS. vol. 95 pp. 14130-14135 (1998).
He and Taussig, "Antibody-ribosome-mRNA(ARM) complexes as efficient selection particles for in vitro display and evolution of antibody combining sites," Nucleic Acids Research. vol. 25, No. 24 pp. 5132-5134 (1997).
Hey et al., "Artificial, non-antibody binding proteins for pharmaceutical and industrial applications," TRENDS in Biotechnology. vol. 23, No. 10 pp. 514-522 (2005).
http://scop.mrc-Imb.cam.ac.uk/scop/data/scop.b.e.ca.html, "Fold: beta-Grasp (ubiquitin-like)," Mar. 15, 2004. [Abstract].
International Preliminary Report on Patentability corresponding to International Patent Application No. PCT/EP2004/005730 dated May 13, 2005. [not in English].
International Search Report corresponding to International Patent Application No. PCT/EP2004/005730 dated Oct. 5, 2004.
International Search Report corresponding to International Patent Application No. PCT/EP2000/006698 dated Feb. 2, 2001.
International Search Report corresponding to International Patent Application No. PCT/EP2005/010932 dated Apr. 11, 2006.
Jackson "Ubiquitin: a small protein folding paradigm." *Org. Biomol. Chem.* vol. 4(10) pp. 1845-1853 (2006).
Jentsch, S., and Pyrowolakis, G., "Ubiquitin and its kin: how close are the family ties?" Trends in Cell Biology. vol. 10 pp. 335-342 (2000).
Khorasanizadeh et al., "Folding and stability of a tryptophan-containing mutant of ubiquitin." *Biochemistry* 32(27): 7054-63 (1993).
Kiel, C., and Serrano, L., "The Ubiquitin Domain Superfold: Structure-based Sequence Alignments and Characterization of Binding Epitopes," J. Mol. Biol. vol. 355 pp. 821-844 (2006).
Knappik et al., "Fully Synthetic Human Combinatorial Antibody Libraries (HuCAL) Based on Modular Consensus Frameworks and CDRs Randomized with Trinucleotides," Journal of Molecular Biology. vol. 296 pp. 57-86 (2000).
Koide et al., "The Fibronectin Type III Domain as a Scaffold for Novel Binding Proteins," Journal of Molecular Biology. vol. 284 pp. 1141-1151 (1998).
Ku, J., and Schultz, P.G., "Alternate protein frameworks for molecular recognition," PNAS. vol. 92 pp. 6552-6556 (1995).

(56) References Cited

OTHER PUBLICATIONS

Larsen et al., "The Ubiquitin Superfamily: Members, Features, and Phylogenies," Journal of Proteome Research. vol. 1 pp. 411-419 (2002).
Laub et al., "Localized solution structure refinement of an F45W variant of ubiquitin using stochastic boundary molecular dynamics and NMR distance restraints," Protein Science. vol. 4 pp. 973-982 (1995).
Lazar, C.N., and Wang, H., "De novo design of the hydrophobic core of ubiquitin," Protein Science. vol. 6 pp. 1167-1178 (1997).
Lipovsek, D., and Pluckthun, A., "In-vitro protein evolution by ribosome display and mRNA display," J. Immunol. Methods. vol. 290 pp. 51-67 (2004).
Mayr et al., "Domain Interactions and Connecting Peptides in Lens Crystallins," Journal of Molecular Biology. vol. 235 pp. 84-88 (1994).
McConnell, S.J., and Hoess, R.H. "Tendamistat as a Scaffold for Conformationally Constrained Phage Peptide Libraries," The Journal of Molecular Biology. vol. 250 pp. 460-470 (1995).
Miura et al., "Characterization of the Binding Interface between Ubiquitin and Class I Human Ubiquitin-conjugating Enzyme 2b by Multidimensional Heteronuclear NMR Spectroscopy in Solution," Journal of Molecular Biology. vol. 290 pp. 213-228 (1999).
Müller et al., "SUMO, ubiquitin's mysterious cousin," Nat. Rev. Mol. Cell Biol. vol. 2 pp. 202-210 (2001).
Müller, H.N., and Skerra, A., "Grafting of a High-Affinity Zn(II)-Binding Site on the β-Barrel of Retional-Binding Protein Results in Enhanced Folding Stability and Enables Simplified Purification," Biochemistry. vol. 33, No. 47 pp. 14126-14135 (1994).
Nord et al., "Binding proteins selected from combinatorial libraries of an (—helical bacterial receptor domain," Nature Biotechnology. vol. 15 pp. 772-777 (1997).
Notice of Allowance corresponding to U.S. Appl. No. 10/030,605 dated Apr. 14, 2009.
Notice of Allowance corresponding to U.S. Appl. No. 11/732,632 dated Aug. 23, 2010.
Notification of Transmittal of Translation of the International Preliminary Report on Patentability (Chapter I of the Patent Cooperation Treaty) corresponding to International Patent Application No. PCT/EP2004/005730 dated Apr. 13, 2006.
Notification of Transmittal of Translation of the International Preliminary Report on Patentability (Chapter I or Chapter II of the Patent Cooperation Treaty) corresponding to International Application No. PCT/EP2005/010932 dated May 3, 2007.
Notification of Transmittal of the International Search Report and the Written Opinion of the International Searching Authority, or the Declaration corresponding to International Patent Application No. PCT/EP2010/069674 dated Jun. 17, 2011.
Nygren, P., and Uhlen, M., "Scaffolds for engineering novel binding sites in proteins," Current Opinion in Structural Biology. vol. 7 pp. 463-469 (1997).
Official Action corresponding to U.S. Appl. No. 12/072,959 dated Jan. 27, 2009.
Official Action corresponding to U.S. Appl. No. 10/030,605 dated Sep. 21, 2004.
Official Action corresponding to U.S. Appl. No. 10/030,605 dated Feb. 15, 2005.
Official Action corresponding to U.S. Appl. No. 10/030,605 dated Aug. 10, 2005.
Official Action corresponding to U.S. Appl. No. 10/030,605 dated Apr. 12, 2006.
Official Action corresponding to U.S. Appl. No. 10/030,605 dated Feb. 28, 2007.
Official Action corresponding to U.S. Appl. No. 10/030,605 dated Nov. 16, 2007.
Official Action corresponding to U.S. Appl. No. 11/656,646 dated Sep. 1, 2009.
Official Action corresponding to U.S. Appl. No. 11/656,646 dated May 25, 2010.
Official Action corresponding to U.S. Appl. No. 10/030,605 dated Jul. 1, 2008.
Official Action corresponding to U.S. Appl. No. 11/656,646 dated Nov. 13, 2009.
Official Action corresponding to U.S. Appl. No. 11/283,332 dated Jan. 9, 2008.
Official Action corresponding to U.S. Appl. No. 11/283,332 dated May 30, 2008.
Official Action corresponding to U.S. Appl. No. 11/283,332 dated Nov. 28, 2008.
Official Action corresponding to U.S. Appl. No. 11/283,332 dated Sep. 4, 2009.
Official Action corresponding to U.S. Appl. No. 12/072,959 dated Jul. 24, 2008.
Official Action corresponding to U.S. Appl. No. 11/283,332 dated Mar. 3, 2010.
Official Action corresponding to U.S. Appl. No. 12/072,959 dated Jan. 5, 2010.
Official Action corresponding to U.S. Appl. No. 11/732,632 dated Jun. 3, 2009.
Official Action corresponding to U.S. Appl. No. 11/732,632 dated Aug. 21, 2009.
Official Action corresponding to U.S. Appl. No. 11/732,632 dated Mar. 19, 2010.
Ohashi et al., "Efficient protein selection based on ribosome display system with purified components," Biochem. Biophys. Res. Commun. vol. 352 pp. 270-276 (2007).
Pack, P., and Pluckthun, A., "Miniantibodies: Use of Amphipathic Helices to Produce Functional, Flexibly Linked Dimeric Fv Fragments with High Avidity in *Escherichia coli*," Biochemsitry. vol. 31, No. 6 pp. 1579-1584 (1992).
Paschke, M., and Höhne, W., "A twin-arginine translocation (Tat)-mediated phage display system," Gene. vol. 350, No. 1 pp. 79-88 (2005).
Richardson et al., "Looking at proteins: representations, folding, packing, and design," Biophysical Journal. vol. 63 pp. 1186-1209 (1992).
Riddle et al., "Functional rapidly folding proteins from simplified amino acid sequences," Nature Structural Biology. vol. 4, No. 10 pp. 805-809 (1997).
Schaffitzel et al., "In Vitro Selection and Evolution of Protein-Ligand Interactions by Ribosome Display," Protein-Protein Interactions, A Molecular Cloning Manual, E. Golemis, Ed. Cold Spring Harbor Laboratory Press, New York. Chapter 30 pp. 535-567 (2001).
Skerra and Plückthun, "Assembly of a Functional Immunoglobulin Fv Fragment in *Escherichia coli*," Science vol. 240 pp. 1038-1041 (1988).
Skerra, "Engineered protein scaffolds for molecular recognition," Journal of Molecular Recognition. vol. 13, No. 4 pp. 167-187 (2000).
Smith et al., "Small Binding Proteins Selected from a Conbinatorial Repertoire of Knottins Displayed on Phage," Journal of Molecular Biology, vol. 277, No. 2 pp. 317-332 (1998).
Stemmer, "Rapid evolution of a protein in vitro by DNA shuffling," Nature. vol. 370 pp. 389-391 (1994).
Wells, "Additivity of Mutational Effects in Proteins," Biochemistry. vol. 29, No. 37 pp. 8509-8517 (1990).
Wells and Lowmann, "Rapid evolution of peptide and protein binding properties in vitro," Current Opinion in Biotechnology. vol. 3 pp. 355-362 (1992).
Winter, "Synthetic human antibodies and a strategy for protein engineering," FEBS Letters. vol. 430 pp. 92-94 (1998).
You, L., and Arnold, F.H., "Directed evolution of subtilisin E in *Bacillus subtilis* to enhance total activity in aqueous dimethylformamide," Protein Engineering, vol. 9, No. 1 pp. 77-83 (1994).
Young et al., "Thermal stabilization of a single-chain Fv antibody fragment by introduction of a disulphide bond," FEBS Letters. vol. 377 pp. 135-139 (1995).
Zahnd et al., "Ribosome display: selecting and evolving proteins in vitro that specifically bind to a target," Nature Methods. vol. 4, No. 3 pp. 269-279 (2007).

(56) References Cited

OTHER PUBLICATIONS

Zhang et al., "Directed evolution of a fucosidase from a galactosidase by DNA shuffling and screening," PNAS. vol. 94 pp. 4504-4509 (1997).
Deed of Grant corresponding to Australian Patent No. 2010332932 dated May 2, 2013.
Deed of Grant corresponding to Australian Patent No. 2010332938 dated Apr. 4, 2013.
Intent to Grant corresponding to European Patent Application No. EP 10 787 815.9-1410 dated Aug. 13, 2013.
International Preliminary Report on Patentability corresponding to International Patent Application No. PCT/EP2004/005730 dated May 13, 2005.
International Preliminary Report on Patentability (Chapter I of the Patent Cooperation Treaty) corresponding to International Patent Application No. PCT/EP2010/069665 dated Jun. 19, 2012.
Notice of Allowance corresponding to U.S. Appl. No. 11/656,646 dated Aug. 27, 2013.
Notification Concerning Transmittal of International Preliminary Report on Patentability (Chapter I of the Patent Cooperation Treaty) corresponding to International Patent Application No. PCT/EP2010/069666 dated Jun. 28, 2012.
Notification Concerning Transmittal of International Preliminary Report on Patentability (Chapter I of the Patent Cooperation Treaty) corresponding to International Patent Application No. PCT/EP2010/069674 dated Jun. 28, 2012.
Official Action corresponding to Chinese Patent Application No. 201080056911.6 dated Jul. 31, 2013.
Official Action corresponding to Korean Patent Application No. 10-2011-7018847 dated Jan. 30, 2013.
Official Action corresponding to U.S. Appl. No. 13/142,195 dated Feb. 11, 2013.
Official Action corresponding to U.S. Appl. No. 13/142,195 dated May 29, 2013.
Search Report corresponding to Chinese Patent Application No. 201080056911.6 dated Jun. 14, 2013.
Hershko, A., and Ciechanover, A., "The Ubiquitin System," Annu. Rev. Biochem. vol. 67 pp. 425-479 (1998).
International Search Report corresponding to International Patent Application No. PCT/EP2007/062375 dated Apr. 25, 2008.
Official Action corresponding to U.S. Appl. No. 11/283,332 dated Sep. 3, 2013.
Official Action corresponding to U.S. Appl. No. 12/072,959 dated Aug. 30, 2013.

\* cited by examiner

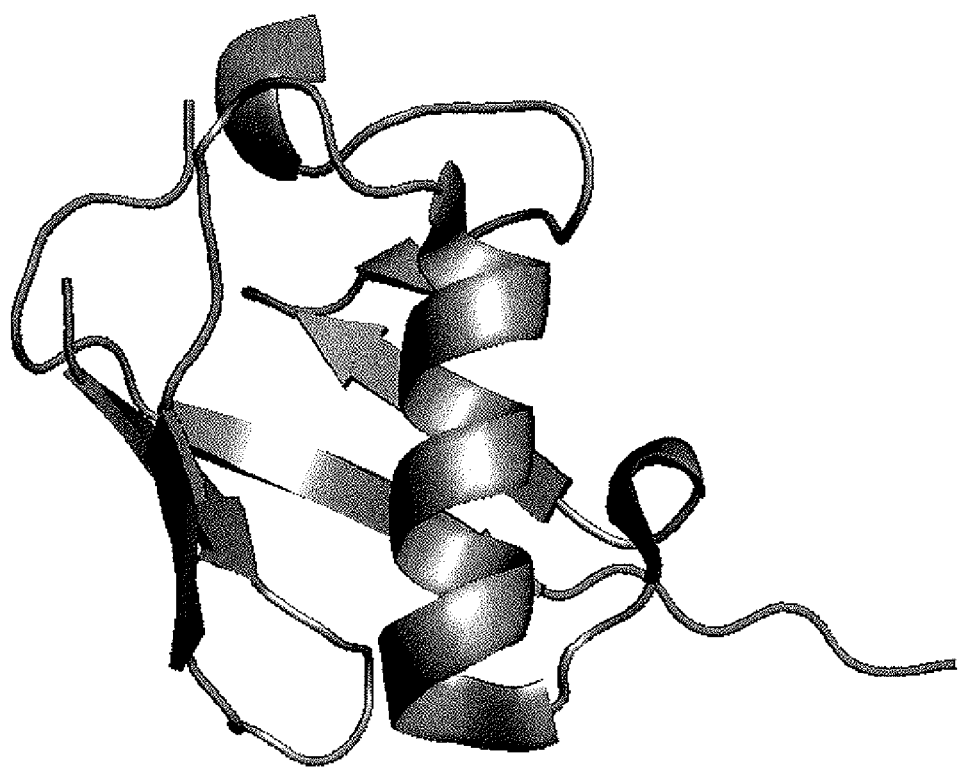
Fig.:1 Ribbon diagram of human wild type ubiquitin. (PDB 1D3Z; Pymol, Version 0.98)

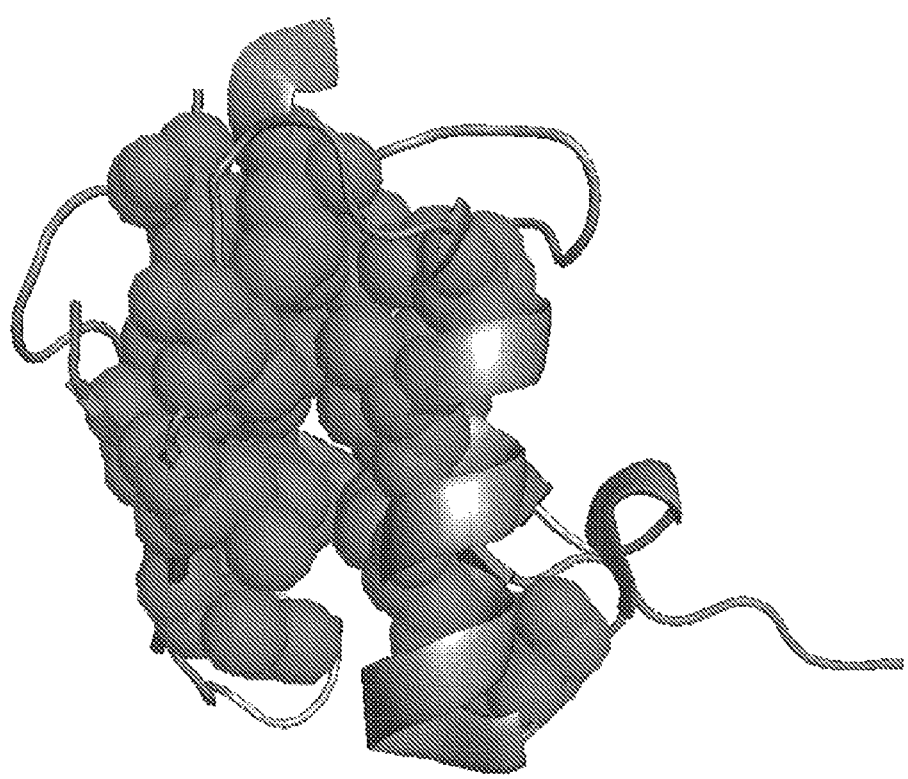
Fig.2: Ribbon diagram of human wild type ubiquitin. (PDB 1D3Z). The amino acids, which assemble the hydrophobic core of the protein are painted as green spheres. (Pymol, Version 0.98).

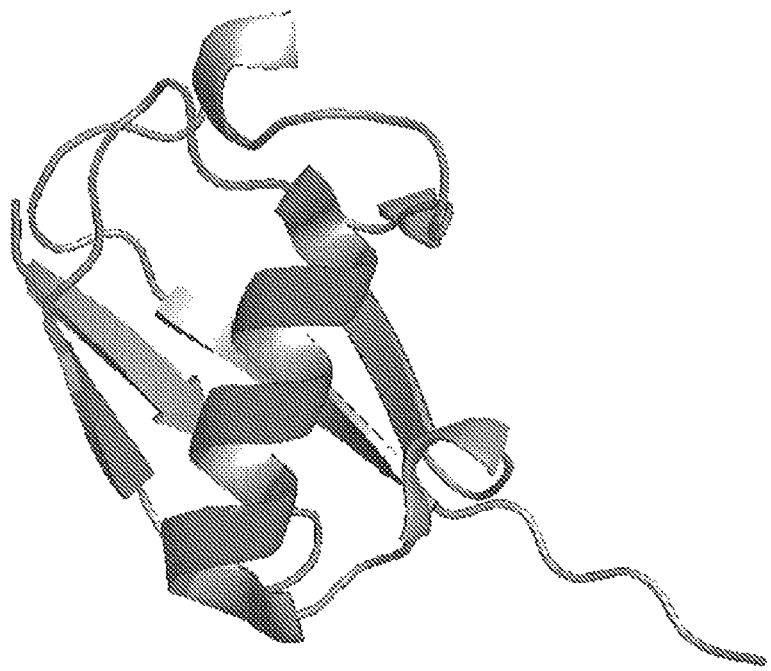
Fig.3: Ribbon diagram of human wild type ubiquitin. (PDB 1D3Z) The amino acids T22, E24, N25, A28, K29, Q31, D32 and K33 belong to the helix (red). The helix-upstream positions E16, E18, S20, D21 are painted in green. The helix downstream positions P38, D39, D52, G53, R54, T55 are painted in orange. The dominating part of the library is the helix. (Pymol, Version 0.98)

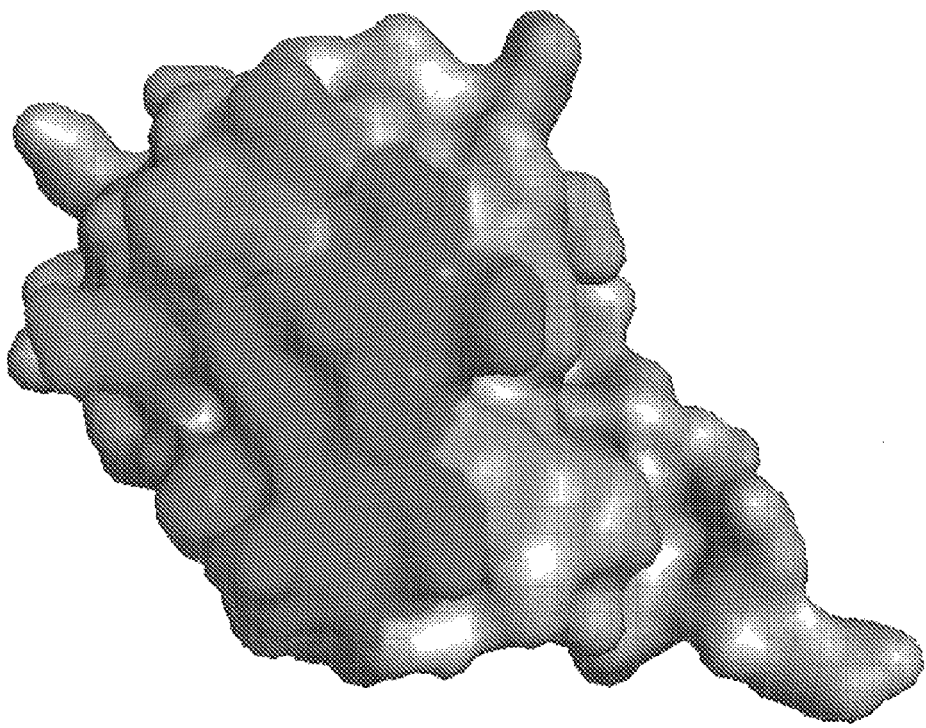
Fig.4: Surface presentation of human wild type ubiquitin. (PDB 1D3Z) The amino acids T22, E24, N25, A28, K29, Q31, D32 and K33 belong to the helix (red). The helix-upstream positions E16, E18, S20, D21 are painted in green. The helix downstream positions P38, D39, D52, G53, R54, T55 are painted in orange. The dominating part of the library is the helix. (Pymol, Version 0.98)

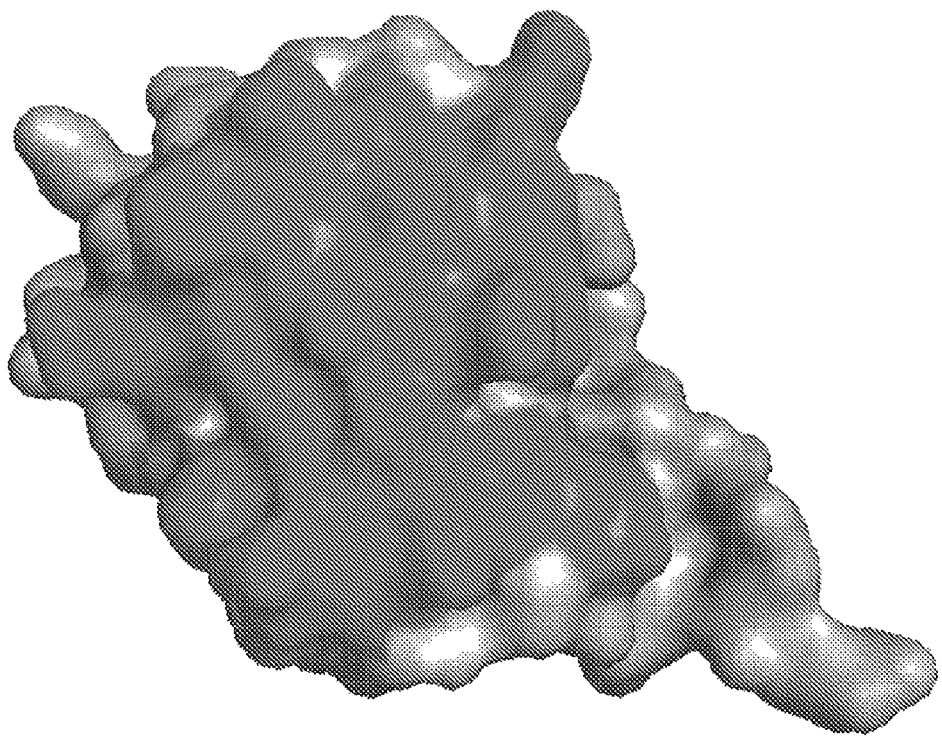
Fig.5: Surface presentation of human wild type ubiquitin. (PDB 1D3Z; Pymol, Version 0.98). The maximum binding site of 1485 Å$^2$ is coloured in red.

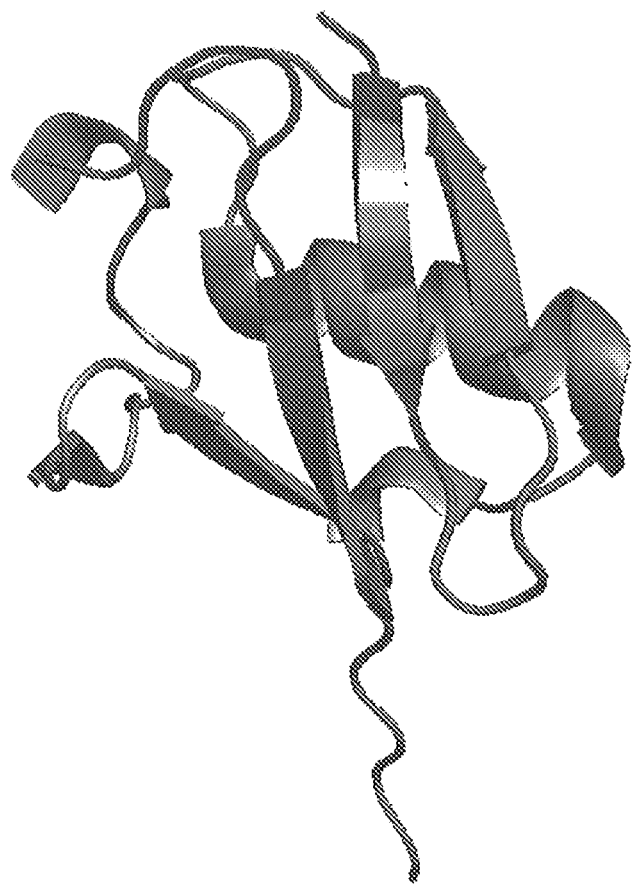
Fig.6: Ribbon diagram of human wild type ubiquitin. (PDB 1D3Z; Pymol, Version 0.98)
The amino acid position, which assemble the sheet-based library are coloured in blue.

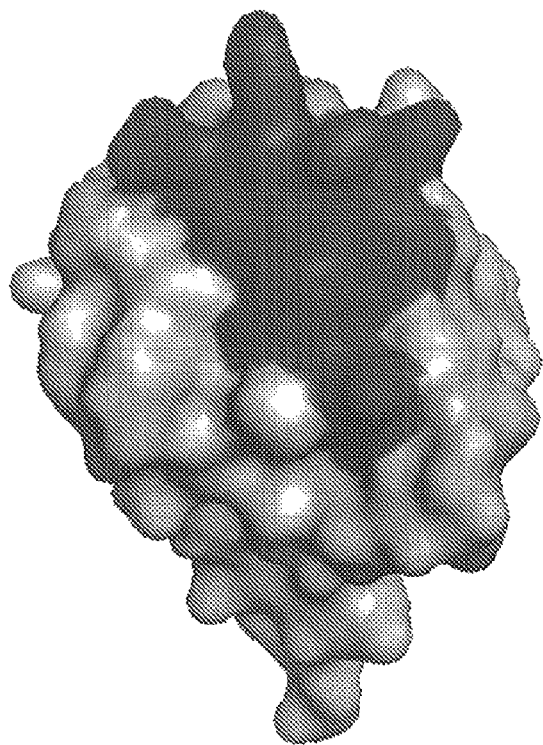
Fig.7: Surface presentation of human wild type ubiquitin. (PDB 1D3Z; Pymol, Version 0.98) The amino acids, which assemble the sheet-based library are coloured in blue.

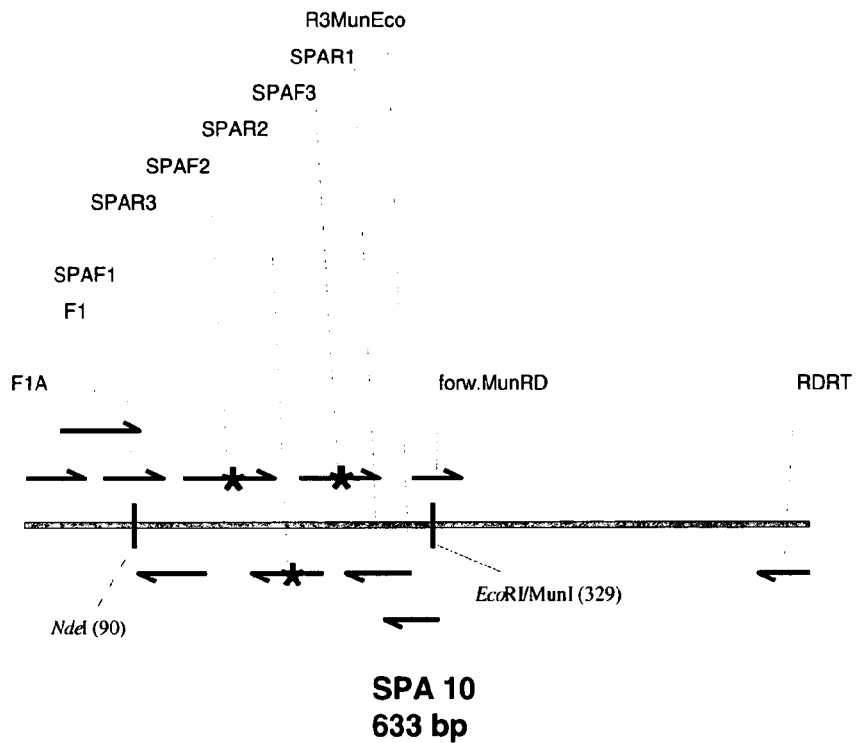

Fig. 8: The ribosome display construct SPA10. Primers are painted as blue arrows. The primers forw.MunRD and R3MunEco were used to generate the restriction sites EcoRI and MunI for the latter restriction ligation of the library fragment and the spacer fragment. The primer RDRT was used for the reverse transcription. The primer pairs F1/RDRT and F1A/RDRT were used for the PCR amplifications during the ribosome display selection procedure. Red crosses mark the primers SPAF2, SPAF3 and SPAR2, which introduce the site directed mutations to generate the library.

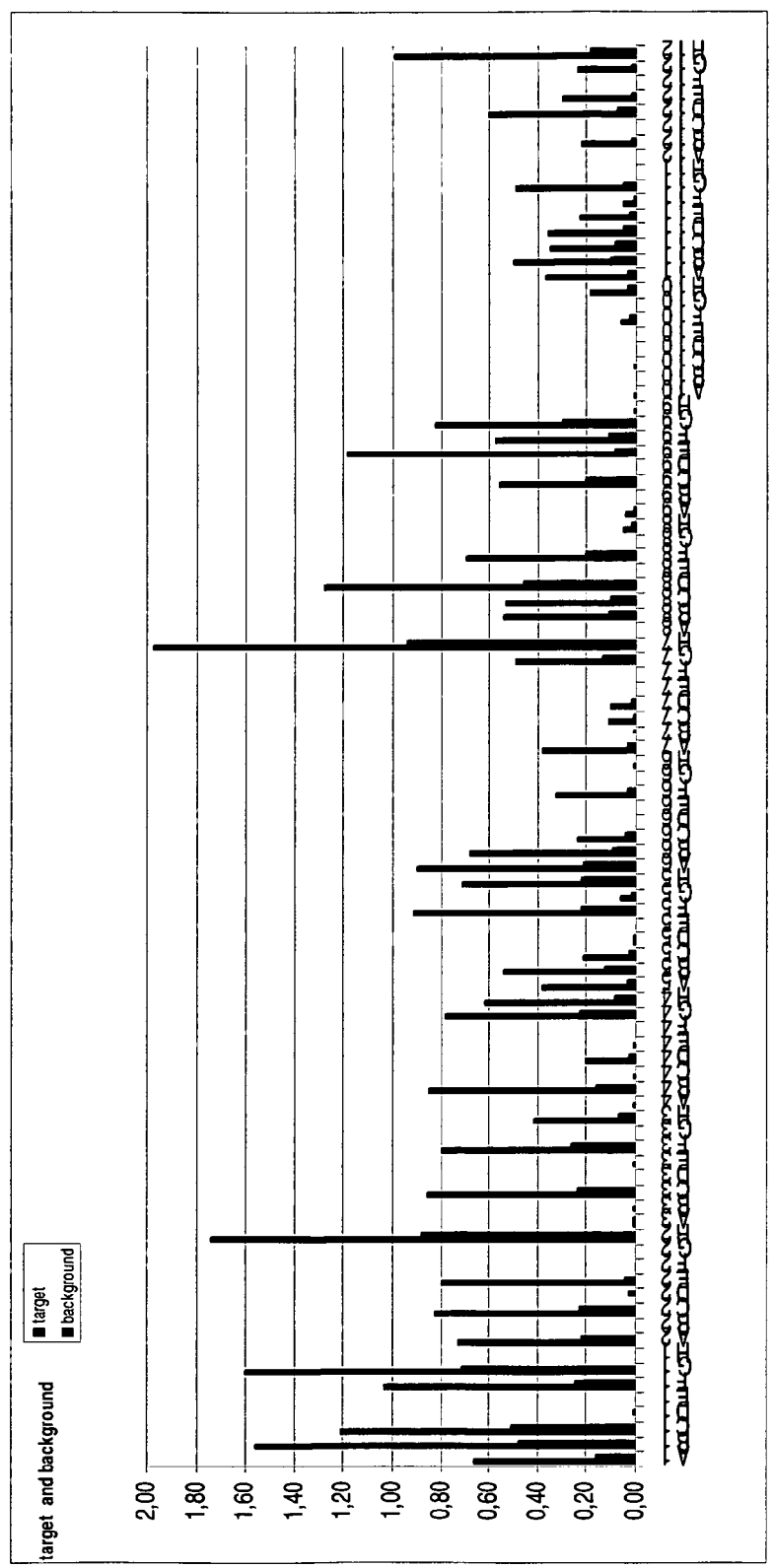
Fig. 9: Exemplary hit-ELISA showing variants of the SPA10 library versus TNFα (red) and BSA (blue) as a background.

MQIFVKTLTGKTITLEVEPNDLIAPVKWKIID■EGIPADQQRLIWAGKQLEDWAGLSD
YNIQKESTLHLVLRLRGGDYKDDDDKGLEHHHHHH

Fig.10: Amino Acid Sequence of the TNFα binding Ubiquitin variant 2E11. 10 substituted amino acid positions are marked in yellow. The position K33 turned into E (red).

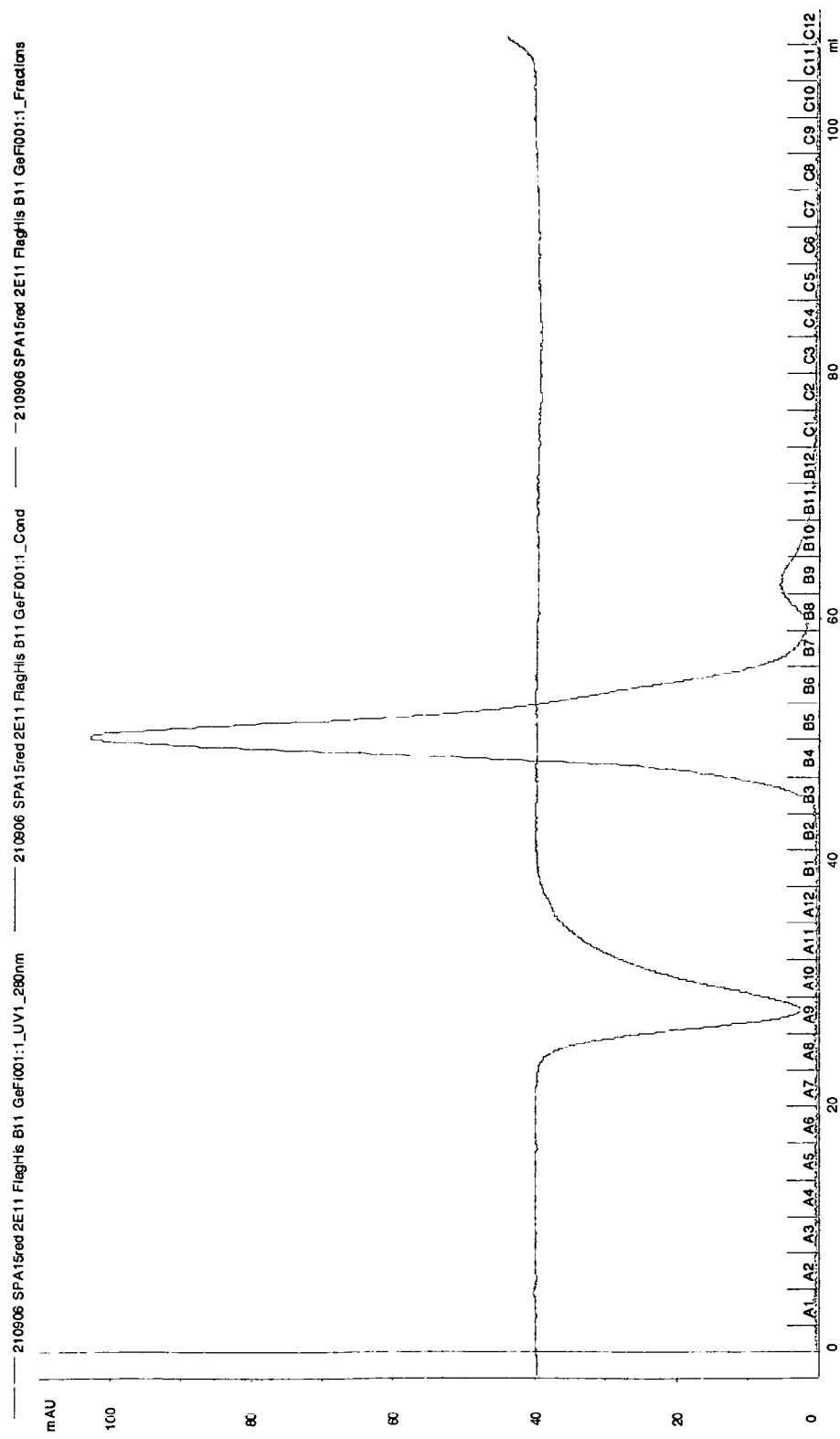
Fig. 11: Chromatography profile of the SEC (Superdex 75, 1.6 x 60, GE Healthcare) during the purification of the ubiquitin variant 2E11. The fraction B5 was used for further binding studies.

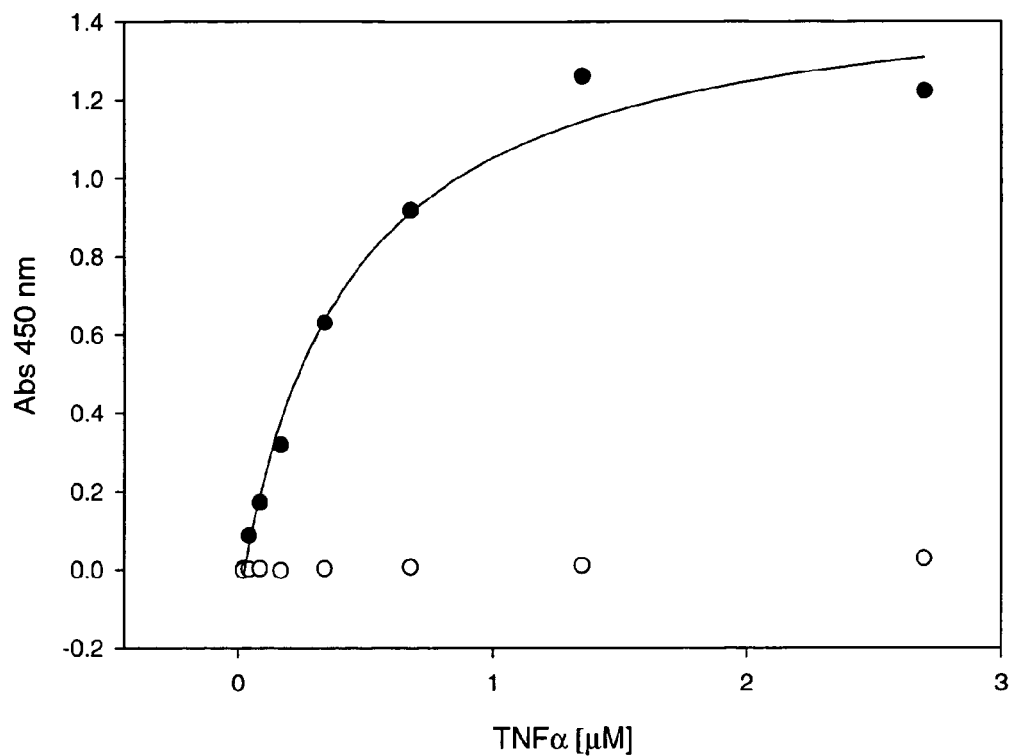
Fig.12: ELISA showing the TNFα concentration-dependant binding characteristics of the SPA14 variant 2E11. Filled circles: Variant 2E11 versus TNFα. Empty circles Variant 2E11 versus BSA. By a non linear sigmoidal curve fitting an apparent affinity was determined of 400 nM (R = 0,99). The fit was created with Sigma Plot (Vers. 6.10)

SEQUENCE LISTING

```
<160> NUMBER OF SEQ ID NOS: 15

<210> SEQ ID NO 1
<211> LENGTH: 49
<212> TYPE: DNA
<213> ORGANISM: Artificial Sequence
<220> FEATURE:
<223> OTHER INFORMATION: Artificially synthesized oligonucleotide Primer
      SPAF1

<400> SEQUENCE: 1
gtttaacttt aagaaggaga tatacatatg cagatttttg tgaaaaccc                49

<210> SEQ ID NO 2
<211> LENGTH: 73
<212> TYPE: DNA
<213> ORGANISM: Artificial Sequence
<220> FEATURE:
<223> OTHER INFORMATION: Artificially synthesized oligonucleotide Primer
      SPAF2
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: k is g or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (28)..(28)
<223> OTHER INFORMATION: k is g or t
```

```
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (34)..(34)
<223> OTHER INFORMATION: k is g or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (37)..(37)
<223> OTHER INFORMATION: k is g or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (46)..(46)
<223> OTHER INFORMATION: k is g or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (55)..(55)
<223> OTHER INFORMATION: k is g or t

<400> SEQUENCE: 2
cactctggaa gtggagcccn nkgacnnkat cnnknnkgtg aagnnkaaga tcnnkgacaa      60
ggagggcatc ccg                                                        73

<210> SEQ ID NO 3
<211> LENGTH: 64
<212> TYPE: DNA
<213> ORGANISM: Artificial Sequence
<220> FEATURE:
<223> OTHER INFORMATION: Artificially synthesized oligonucleotide Primer
      SPAF3
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (28)..(28)
<223> OTHER INFORMATION: k is g or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (31)..(31)
<223> OTHER INFORMATION: k is g or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (34)..(34)
<223> OTHER INFORMATION: k is g or t

<400> SEQUENCE: 3
ctgggcgggt aaacagctcg aagacnnknn knnkctgagc gattacaaca tccagaaaga      60
aagc                                                                  64
```

<210> SEQ ID NO 4
<211> LENGTH: 52
<212> TYPE: DNA
<213> ORGANISM: Artificial Sequence
<220> FEATURE:
<223> OTHER INFORMATION: Artificially synthesized oligonucleotide Primer
      SPAR1

<400> SEQUENCE: 4
cgcagacgca gcaccagatg cagggtgctt tctttctgga tgttgtaatc gc         52

<210> SEQ ID NO 5
<211> LENGTH: 58
<212> TYPE: DNA
<213> ORGANISM: Artificial Sequence
<220> FEATURE:
<223> OTHER INFORMATION: Artificially synthesized oligonucleotide Primer
      SPAR2
<220> FEATURE:
<221> NAME/KEY: misc_feature
<222> LOCATION: (38)..(38)
<223> OTHER INFORMATION: m is a or c
<220> FEATURE:
<221> NAME/KEY: misc_feature
<222> LOCATION: (39)..(40)
<223> OTHER INFORMATION: n is a, c, g, or t

<400> SEQUENCE: 5
cgagctgttt acccgcccag atcagacgct gctgatcmnn cgggatgccc tccttgtc   58

<210> SEQ ID NO 6
<211> LENGTH: 55
<212> TYPE: DNA
<213> ORGANISM: Artificial Sequence
<220> FEATURE:
<223> OTHER INFORMATION: Artificially synthesized oligonucleotide Primer
      SPAR3

<400> SEQUENCE: 6
gggctccact tccagagtga tggtcttgcc ggtcagggtt ttcacaaaaa tctgc      55

<210> SEQ ID NO 7
<211> LENGTH: 65
<212> TYPE: DNA
<213> ORGANISM: Artificial Sequence
<220> FEATURE:
<223> OTHER INFORMATION: Artificially synthesized oligonucleotide Primer
      F1

<400> SEQUENCE: 7
ggagaccaca acggtttccc tctagaaata attttgttta actttaagaa ggagatatac    60
atatg                                                                65

<210> SEQ ID NO 8
<211> LENGTH: 43
<212> TYPE: DNA
<213> ORGANISM: Artificial Sequence
<220> FEATURE:
<223> OTHER INFORMATION: Artificially synthesized oligonucleotide Primer
      R3MunEco

<400> SEQUENCE: 8
gaattcacta cctccgccgc cacgcagacg cagcaccaga tgc                  43

<210> SEQ ID NO 9
<211> LENGTH: 48
<212> TYPE: DNA
<213> ORGANISM: Artificial Sequence

```
<220> FEATURE:
<223> OTHER INFORMATION: Artificially synthesized oligonucleotide Primer
      F1A

<400> SEQUENCE: 9
catacgaaat taatacgact cactataggg agaccacaac ggtttccc                48

<210> SEQ ID NO 10
<211> LENGTH: 315
<212> TYPE: DNA
<213> ORGANISM: Artificial Sequence
<220> FEATURE:
<223> OTHER INFORMATION: Artificially synthesized Ribosome Display
      spacer

<400> SEQUENCE: 10
ggaggtagtc aattggctgg ctctggagct ggtgcaggct ctggtgctgg cgcaggttct      60
ggcgctggtg ctggttctgg cactggtgct ctccggcag ctgttccggc agcggttcca     120
gcagcggtgc cggcagcagt tcctgctgcg gtgggcgaag agaaggaga aggcgaggga     180 gagggcgaag ataccccgta cgacgtaccg gactacgccg aaggtggtgg tggctccgag    240
cagaagctca tctccgaaga agacctggag ggtggtggtg gctccacaga ctacaaggac    300
gacgacgaca aatcc                                                     315

<210> SEQ ID NO 11
<211> LENGTH: 39
<212> TYPE: DNA
<213> ORGANISM: Artificial Sequence
<220> FEATURE:
<223> OTHER INFORMATION: Artificially synthesized oligonucleotide Primer
      forw.MunRD

<400> SEQUENCE: 11
ggcggcggag gtagtgaatt cgctggctct ggagctggt                             39

<210> SEQ ID NO 12
<211> LENGTH: 42
<212> TYPE: DNA
<213> ORGANISM: Artificial Sequence
<220> FEATURE:
<223> OTHER INFORMATION: Artificially synthesized oligonucleotide Primer
      RDRT

<400> SEQUENCE: 12
ggatttgtcg tcgtcgtcct tgtagtctgt ggagccacca cc                         42

<210> SEQ ID NO 13
<211> LENGTH: 61
<212> TYPE: DNA
<213> ORGANISM: Artificial Sequence
<220> FEATURE:
<223> OTHER INFORMATION: Artificially synthesized oligonucleotide Primer
      WubiFlagXhoIrv

<400> SEQUENCE: 13
ccattccacc tcgagaccct tatcatcatc atctttgtaa tcgccgccac gcagacgcag      60
c                                                                     61

<210> SEQ ID NO 14
<211> LENGTH: 93
<212> TYPE: PRT
<213> ORGANISM: Artificial Sequence
<220> FEATURE:
<223> OTHER INFORMATION: Artifical ubiquitin variant 2E11
```

```
<400> SEQUENCE: 14

Met Gln Ile Phe Val Lys Thr Leu Thr Gly Lys Thr Ile Thr Leu Glu
1               5                   10                  15

Val Glu Pro Asn Asp Leu Ile Ala Pro Val Lys Trp Lys Ile Ile Asp
            20                  25                  30

Glu Glu Gly Ile Pro Ala Asp Gln Gln Arg Leu Ile Trp Ala Gly Lys
        35                  40                  45

Gln Leu Glu Asp Trp Ala Gly Leu Ser Asp Tyr Asn Ile Gln Lys Glu
    50                  55                  60

Ser Thr Leu His Leu Val Leu Arg Leu Arg Gly Gly Asp Tyr Lys Asp
65                  70                  75                  80

Asp Asp Asp Lys Gly Leu Glu His His His His His His
                85                  90

<210> SEQ ID NO 15
<211> LENGTH: 76
<212> TYPE: PRT
<213> ORGANISM: Homo sapiens

<400> SEQUENCE: 15

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```

ARTIFICIAL BINDING PROTEINS BASED ON A MODIFIED ALPHA HELICAL REGION OF UBIQUITIN

The present invention is directed to binding proteins derived from the protein superfamily of ubiquitin like proteins with modifications in their alpha helical region. The present invention is further directed to a method for the generation of those proteins as well as to a protein obtainable by said method. Furthermore, the invention provides the use of a protein for the specific recognition, binding and neutralization of a predescribed target molecule, for the detection, quantitative determination, separation and/or for the isolation of a corresponding binding partner and the use of a protein of the invention, for diagnosis, prophylaxis and treatment of diseases in which the corresponding binding partner is directly or indirectly involved.

BACKGROUND OF THE INVENTION

Ubiquitin is a small, monomeric, and cytosolic protein which is highly conserved in sequence and is present in all known eukaryotic cells from protozoans to vertebrates. In the organism, it plays a crucial role in the regulation of the controlled degradation of cellular proteins. For this purpose, the proteins destined for degradation are covalently linked to ubiquitin or polyubiquitin chains during their passage through a cascade of enzymes and are selectively degraded because of this label. According to recent results, ubiquitin or the labelling of proteins by ubiquitin, respectively, plays an important role also in other cellular processes such as the import of several proteins or the gene regulation thereof (Marx, 2002).

Besides the clarification of its physiological function, ubiquitin is a research object primarily because of its structural and proteinchemical properties. The polypeptide chain of ubiquitin consists of 76 amino acids folded in an extraordinarily compact alpha/beta structure (Vijay-Kumar, 1987): almost 87% of the polypeptide chain are involved in the formation of the secondary structural elements by means of hydrogen bonds. As prominent secondary structures can be mentioned three and a half alpha-helical turns as well as an antiparallel beta-sheet consisting of four strands. The characteristic arrangement of these elements—an antiparallel beta sheet exposed to the protein surface onto the back side of which an alpha helix is packed which lies vertically on top of it—is generally considered as so-called ubiquitin-like folding motif. Therefore, ubiquitin is name-giving for the respective protein superfamily ("ubiquitin-like proteins") or the protein family ("ubiquitin-related proteins"), respectively, (Murzin et al., 1995) which comprises proteins such as for example SUMO-1 (Müller et al., 2001), FAU (Michiels et al., 1993), NEDD-8 (Kumar et al., 1993), UBL-1 (Jones and Candino, 1993), and GDX (Filippi et al., 1990) bearing this motif as well as a high degree of identity to ubiquitin in their primary sequence.

Human Ubiquitin is—as mentioned above—a 76 amino acid long polypeptide (FIG. 1). It is a small, globular protein of 7.5 kDa with an extruding C-terminus. The main structural features of ubiquitin are shown in FIG. 1. Hydrophobic residues from the sheet and from the helix assemble the hydrophobic core of the protein and stabilize the orientation of the helix (FIG. 2). The highly dense hydrophobic packing of the protein's core is reflected by its excellent thermodynamic stability, which should make the protein to an ideal candidate to use it as a scaffold for protein engineering approaches.

Because of its small size, the artificial preparation of ubiquitin can be carried out both by chemical synthesis and by means of biotechnological methods. Due to the favourable folding properties, ubiquitin can be produced by genetic engineering using microorganisms such as *Escherichia coli* in relatively large amounts either in the cytosol or in the periplasmic space. Because of the oxidizing conditions predominating in the periplasm the latter strategy generally is reserved for the production of secretory proteins. Due to the simple and efficient bacterial preparation ubiquitin can be used as a fusion partner for other foreign proteins to be prepared for which the production is problematic. By means of the fusion to ubiquitin an improved solubility and thereby an improved yield can be achieved. The approach practised in the present invention to provide ubiquitin as universal artificial binding protein allows for a completely novel utilization of its proteinchemical properties.

Among those proteins of which the natural function is utilized in diagnostics and pharmaceutics the immunoglobulins play a predominant role. Their ability of specific, non-covalent binding to a wide range of different substances makes them the most important tool for bioscientific application. The methods developed in recent years for the functional biosynthesis of antibody fragments in *E. coli* have further extended the possibilities using immunoglobulins but have at the same time demonstrated their limitations.

Besides Fab- and Fv-fragments (Skerra and Plückthun, 1988) which principally can be obtained by conventional methods, different artificial constructs could be developed by means of protein engineering methods. Assisted by the modular structure of immunoglobulins (reviewed in Düthel and Kontermann, 2001), notably single chain Fv fragments (scFv) (Bird et al., 1988), disulfide-bridged Fv fragments (dsFv) (Brinkmann et al., 1993) as well as bivalent (Carter et al., 1992) and bispecific antibody fragments (e.g. diabodies, Holliger et al., 1993) could be generated. For diagnosis and the use in therapy bifunctional proteins can be obtained by genetic fusion of the recombinant Ig fragments to effector modules. Thus, fusions to alkaline phosphatase (Müller et al., 1999) and the green fluorescent protein (GFP; Griep et al., 1999) are available among others. Fusions of antibody fragments to radioisotopes or cytotoxic substances are of great potential importance for cancer treatment (immunotoxins; Reiter and Pastan, 1998). In this case, the selective binding of respective Ig fragments to specific surface proteins on tumor cells is utilized for the site-specific application of therapeutics (tumor targeting).

However, the methods for the preparation of antibody fragments in *E. coli* not only allow for their provision for diagnostics and therapy in sufficient quality and quantity but also for simple and quick modification of their protein- and immunochemical properties. The easy handling of a bacterial host enables a straightforward alteration of the vector-encoded genes for the foreign protein by means of standard molecular-biological methods. By means of a targeted antibody engineering (Kontermann and Dübel, 2001) antibody fragments can thus be optimised e.g. with respect to their binding affinity or their host compatibility. Also, specific antibodies or fragments thereof, respectively, can be prepared artificially, i.e. out of the immune system, which are directed against the most different target substances such as low molecular weight structures or proteins for example. By such evolutive methods synthetic libraries of antibody fragments are prepared by the introduction of random mutations which in their extent can be close to the human repertoire (Knappik et al., 2000). By means of suitable selection strategies such as phage display or ribosome display (Winter, 1998, Hoogenboom et al., 1998;

Hanes et al., 2000) functional Ig fragments having the desired binding property are isolated in the case of success. In this manner it is also possible for example to obtain binding proteins for such antigens which during a classical immunization would provoke toxic effects or only a weak immune response.

Despite the above-mentioned achievements and possibilities provided by antibody engineering certain disadvantages can limit the practical use of antibodies. Thus, it is a problem to provide them in sufficient amounts.

The production of functional antibodies is carried out primarily in eukaryotic cell culture systems, which is an extraordinarily cost-intensive method. Furthermore, the low tissue penetration of the antibody molecules due to their size and their long residence time in the serum (slow blood clearance), respectively, hamper many therapeutic applications. Although smaller fragments of antibodies such as scFv or Fab fragments (see above) can be prepared in bacteria and thus basically at lower costs the yields of this recombinant production, however, are lower than the desired level due to their unfavourable folding properties and the required formation of several disulfide bonds. Moreover, recombinant antibody fragments often show a reduced thermodynamic stability, a lower binding activity and higher aggregation tendencies, as compared to the parental antibodies. In order to circumvent such limitations attempts have been made to impart the principle of antibody binding—namely the binding by means of a hypervariable surface-exposed region localized on a conserved protein scaffold—to other proteins (Skerra, 2000). This means that essentially variable loops are varied in order to generate an artificial binding property. For this purpose, usually natural binding proteins such as e.g. lipocalins (Beste et al., 1999) or the fibronectin type III domain (Koide et al., 1998) have been used as a starting point for which binding sites are formed in a manner analogously to antibodies from flexible "loop" structures whose modification enables the induced fit recognition of ligands.

WO2004/106368 relates to modified proteins of the superfamily of "ubiquitin-like proteins", proteins that have a ubiquitin-like fold. As a result of said modification, the proteins have a binding affinity with respect to a predetermined binding partner that did not exist previously. The invention also relates to a method for the production and utilization of said proteins. According to WO2004/106368 a protein is provided selected from the group consisting of proteins of the protein superfamily of "ubiquitin-like proteins" wherein due to one or more modifications of amino acids in the beta sheet strand of the beta sheet region the protein shows a modified binding affinity. Thus, a de novo binding site on human ubiquitin was assembled out of new amino acid substitutions at the positions Q2, F4, K6, Q62, K63, E64, S65 and T66 (FIG. 6, 7).

Unfortunately, due to the close proximity of the de novo binding site to the N-terminus of the protein, the codon composition of the newly introduced amino acids resulted in inhomogeneous expression rates of the protein variants and severely constricted a subsequent N-terminal genetic fusion or posttranslational N-terminal labeling of the variants. Finally, the development of high affinity binding polypeptides using the convex beta sheet topology as a paratope was dependent on the presence of a concave structure of the target molecule.

SUMMARY OF THE INVENTION

Therefore, it is an object of the present invention to provide modified proteins having novel and/or improved binding affinities that did not exist previously (compared to the wild type protein) to selected binding partners or target molecules without showing the disadvantages described above, i.e. which can be used also for other target molecules than those having a concave structure. Another object of the present invention is to create substitute molecules for antibodies which, however, do not show the above-mentioned disadvantages of antibodies.

Furthermore, it is an object of the present invention to provide respective methods for the preparation of the above-mentioned ubiquitin-based modified proteins and uses for these modified proteins.

The above objects are achieved by the subject-matter of the independent claims. Preferred embodiments are set forth in the dependent claims.

To overcome the limitations of the beta sheet-based library strategy a new approach was used to generate an alternative binding-site on the ubiquitin surface. In the almost convex topology of this globular protein the alpha helix of the wild type ubiquitin exceptionally exhibits a solvent exposed, planar topology of about 750 $Å^2$, which at a first glance seems rather inapplicable for the generation of a new binding site. However, it unexpectedly turned out that the helix may serve as an excellent base for the generation of new and modified ubiquitin molecules having a binding affinity to predetermined binding partners.

The present approach was based on the presumption that the ubiquitin alpha helix could be mutagenized without a perturbation of the stabilizing hydrophobic core and—even more important—the folding pathway of ubiquitin. This was in a total contrast to the fact that the helix of ubiquitin plays a central role in the folding-pathway of the protein. During the translation of ubiquitin the first two strands of ubiquitin elongate from the ribosome and rapidly fold into a two-stranded sheet, which is in itself a stable structure (Bofill and Searle 2005). Theoretically, this small sheet then serves as a backbone template for the helix. The sheet and the helix form the transition state of the protein during its folding pathway (Crespo, Simpson et al. 2006; Jackson 2006; Pandit, Jha et al. 2006). The rest of the polypeptide chain subsequently folds through collision with this complex.

Therefore, mutations in the transition state complex of ubiquitin should severely influence the folding pathway of the protein. It could be expected that the solubility, the stability and the overall structural integrity of the mutated protein is severely limited by such an approach.

In the present invention, an exemplary result is illustrated, which, very astonishingly has shown, that a high affinity ubiquitin-derived, monomeric binding variant could be produced by a mutational approach using the alpha helix of ubiquitin as a core structure. Moreover, by this approach, the N-terminus of the protein remains free from mutations, which enables a homogenous expression yield of sequence heterologous variants via a codon-optimized DNA sequence of the first 19 amino acids. N-terminal genetic fusions as well as subsequent labeling approaches furthermore became possible.

DETAILED DESCRIPTION OF THE INVENTION

The present invention in a main aspect is directed to a method for the generation of a protein selected from the group consisting of proteins of the protein superfamily of "ubiquitin-like proteins", proteins having an ubiquitin-like folding motif as well as fragments or fusion proteins thereof each of which having the ubiquitin-like folding motif, wherein the protein due to one or more modifications of amino acids in the alpha helical region show an improved binding affinity with respect to an agent which binding affinity did not exist or did not exist to that extent in the unmodified protein.

Furthermore, the present invention provides a protein selected from the group consisting of proteins of the protein superfamily of "ubiquitin-like proteins" each having an ubiquitin-like folding motif as well as fragments or fusion proteins thereof each having the ubiquitin-like folding motif and the following characteristics:

the protein due to modifications of those amino acids forming the alpha helical region of the protein has a new or enhanced binding affinity with respect to a predetermined binding partner (agent);

the binding affinity did not exist or did not exist to that extent in the unmodified protein; and at least four surface-exposed amino acids in the alpha helix or adjacent regions are modified.

improved binding affinities to a predetermined binding partner could be enhanced, if at least four surface-exposed amino acids in the alpha helix or adjacent regions are modified.

It is noted that in order to establish a non-transient protein-protein interaction, a sufficient surface-exposed area is required, which is assembled from amino acid residues, which, as a matter of course, participate in such an interaction. It is assumed that four surface-exposed amino acids are the absolute minimum to generate such an interaction. In order to establish this interaction more efficiently, it is preferred that the number of surface-exposed amino acids is being at least 6, more preferably at least 8. It is further preferred that the exposed amino acids in the alpha helix or adjacent regions are providing a solvent accessible surface area of at least 400 $Å^2$ more preferably 600 $Å^2$. Examples for those surface accessible surface areas are indicated in Table 1:

TABLE 1

Calculation of SASA (Surface Accessible Surface Area) of ubiquitin (PDB 1UBQ) by means of PyMOL version 0.98.

| amino acids | Amino acid position | $Å^2$ |
|---|---|---|
| 4 | T22, E24, N25, A28 | 266.814 |
| 6 | T22, E24, N25, A28, Q31, D32 | 473.884 |
| 8 | D21, T22, E24, N25, A28, Q31, D32, P38 | 544.976 |
| 10 | S20, D21, T22, E24, N25, A28, K29, Q31, D32, P38 | 711.029 |
| 12 | S20, D21, T22, E24, N25, A28, K29, Q31, D32, P38, D52, G53 | 847.595 |
| 14 | S20, D21, T22, E24, N25, A28, K29, Q31, D32, P38, D52, G53, R54, T55 | 1010.998 |
| 16 | E16, E18, S20, D21, T22, E24, N25, A28, K29, Q31, D32, P38, D52, G53, R54, T55 | 1239.035 |
| 18 | E16, E18, S20, D21, T22, E24, N25, A28, K29, Q31, K33, D32, P38, D39, D52, G53, R54, T55 | 1484.749 |

Thus, the invention provides proteins or polypeptides, respectively, prepared by modification of proteins or polypeptides, respectively, having an ubiquitin-like folding motif as defined in the present application. These include the proteins of the protein superfamily of "ubiquitin-like-proteins", all proteins having an ubiquitin-like folding motif and fragments or fusion proteins of these proteins, with the proviso that they also have an ubiquitin-like folding motif. Starting from these proteins or polypeptides, respectively, at least four surface-exposed amino acids in the alpha helix region of the original protein or polypeptide, respectively, are modified. These modifications particularly comprise the substitution of amino acids, but also insertions and deletions of one or more amino acids as well as chemical modifications of amino acids.

It is noted that the term "alpha helical region" as used herein is meant to comprise the three alpha-helical turns in the ubiquitin-like fold. With regard to human ubiquitin the positions from T22 to D32 belong to the helical core region of ubiquitin. This term, however, also encompasses the amino acids 16-21 (helix upstream positions) and 38-55 (helix downstream positions) lying outside the alpha helix. Or in other words, the term "alpha-helical region" is being equivalent to the expression "alpha helix or adjacent regions" as used herein.

The modification of the at least four amino acids in the alpha helical region means that the amino acid should be localized at the surface of the protein to be accessible for the binding partner or the ligand, respectively, able to bind to the modified protein with an affinity which can be determined.

Thus, according to the invention, at least four surface-exposed amino acids in the alpha helix or adjacent regions are modified. It turned out that the likelihood of new and/or For further information, it is referred to Fletcher, S. and A. D. Hamilton (2005). "Protein surface recognition and proteomimetics: mimics of protein surface structure and function." *Curr Opin Chem Biol* 9(6): 632-8.

It is noted that the proteins of the present invention preferably carry modifications regarding the wild type (wt) protein in their alpha-helical region only. However, modifications lying outside the above defined range, which additionally can contribute to the overall stability, folding efficacy, solubility, target-specificity or affinity are encompassed according to an embodiment.

This implicates further strategies to maturate a ubiquitin binding variant by means of random mutagenesis (e.g. Error-Prone PCR), by site-directed rerandomization of positions within the preselected binding cassette, by targeted single amino acid substitutions or by chemical modifications. Different techniques known per se for the modification of one or more amino acids are available to those skilled in the art. These will be described in more detail in the following. In addition, reference is made to the publications of Ausubel et al., 1994, as well as Sambrook et al., 1989.

Modifications of amino acids of the non-surface-exposed core region of ubiquitin are already known (Finucane et al., Biochemistry, vol. 38, No. 36, 1999 or Lazar et al., Protein Science (1997), 6: 1167-1178). The alterations made therein are directed to positions not involved in binding which due to their localization within the hydrophobic core are not accessible to the solvent or to possible binding partners.

In the following, the meaning of the term "binding affinity that did not exist or did not exist to that extent in the unmodified protein" and de novo generated artificial binding site, respectively, in the context of this invention shall be explained. These terms mean that the modified protein previously shows no or little binding property to a predetermined binding partner. In another embodiment of the invention the proteins to be modified are selected to have no binding affinity to the predetermined binding partner. The binding partners which can also be defined as ligands have a measurable affinity to the protein modified according to the invention. As a minimal value for the presence of a quantifiable binding property, i.e. the affinity with which the partner is bound, can be considered according to the invention a equilibrium constant for the complex formed of $K_D=10^{-5}$ M or smaller. A value of $10^{-5}$ M and below can be considered as a quantifiable binding affinity. Depending on the application a value of $10^{-6}$ M to $10^{-12}$ M is preferred, further preferably $10^{-7}$ to $10^{-11}$ M for e.g. chromatographic applications or $10^{-9}$ to $10^{-12}$ M for e.g. diagnostic or therapeutic applications. Further preferred binding affinities are in the range of $10^{-8}$ to $10^{-10}$ M, preferably to $10^{-11}$ M. The methods for the determination of the binding affinities are known per se and are further described on the following pages.

The term "modification" according to the invention is intended to mean substitutions of amino acids, insertions, deletions or chemical modifications.

As proteins to be modified according to the invention proteins of the superfamily of "ubiquitin-like proteins" can be used. According to the invention, this superfamily comprises the subgroups listed in Murzin et al. (1995). These include for example the protein families of "ubiquitin-related proteins", "UBX domain", GABARAP-like", RAS-binding domain", etc. Preferably, proteins of the protein family of "ubiquitin-related proteins" are used. According to the invention also those proteins are comprised which have an ubiquitin-like folding motif. Examples of these are SUMO-1, FAU, NEDD-8, UBL-1, and GDX as well as Rub1, APG8, ISG15, URM1, HUB1, elongin B, PLIC2 (N-terminal domain), human parkin (N-terminal domain).

The proteins which may be used according to the invention from the superfamily of ubiquitin-like proteins have been characterized to a high extent. Accordingly, the family of ubiquitin-like proteins is defined as a superfamily to which the family of ubiquitin-related proteins belongs. A characteristic of the members of the ubiquitin-like proteins thus is an antiparallel β sheet exposed to one surface of the protein onto the back side of which an a helix is packed which lies perpendicularly on top of it. This ubiquitin-like folding motif is a characteristic of the proteins which can be used and modified according to the invention and clearly distinguishes the members of the family from other proteins. In view of this definition, also the ubiquitin-like N-terminal domain of PLIC-2 and the ubiquitin-like domain of parkin are comprised by the invention.

Those skilled in the art can preliminarily judge either with respect to sequence comparisons, so-called alignments, or by structural considerations whether the proteins are a member of the protein superfamily of ubiquitin-like proteins or not. Naturally, the last evidence is always provided by a structural analysis, for example a structural analysis by X-ray crystallography or multidimensional nuclear magnetic resonance spectroscopy. In recent times, also structural analysis using genetic algorithms can provide good predictions.

The proteins of the above-mentioned family and superfamily usually are highly conserved. According to present knowledge, ubiquitin for example has an identical amino acid sequence in all mammals. Ubiquitin of yeast differs only in three amino acids from this sequence. Human ubiquitin or ubiquitin of mammals, respectively, consists of 76 amino acids and has the structure described in the beginning.

The following embodiments are directed to the method aspect and the protein aspect of the present invention:

According to the invention, the modified protein should have at least 30%, preferably at least 40% or 50%, further preferably at least 60%, at least 70%, at least 80%, at least 90%, or at least 95% identity in its amino acid sequence to the starting protein which is modified, for example to human ubiquitin wherein the protein in any case has an ubiquitin-like folding motif as defined in detail above.

According to the invention, also fragments of the proteins mentioned are comprised as long as they comprise the ubiquitin-like folding motif described above, as well as fusions of the proteins mentioned to other proteins. In the case of such fragments and fusion proteins, amino acid positions mentioned in the frame of the invention refer to the respective position in human ubiquitin. Examples of fusion partners are (reporter) enzymes, toxins, proteases, proteins which prolong or reduce the half-life of the construct or other binding proteins etc. Furthermore, chemical coupling for example to low molecular weight substances such as biotin, digoxigenin, fluorescent and/or luminescent substances etc. can be performed.

According to a still preferred embodiment, the protein is linked in a site-specific and covalent manner to a protein of the same or a different specificity and thus shows bivalent or bispecific binding properties, respectively.

In the case of generating fusion proteins, a fragment of the construct or all fusion partners can be modified according to the invention. It is also comprised by the invention, however, that a segment is fused, followed by a modification method, which can comprise a posttranslational modification, an affinity, stability or solubility maturation or a further selection for binding to the primary target or versus a second target molecule. In each case this can be done according to methods known to those skilled in the art.

More detailed information regarding how to generate and to use fusion proteins or conjugates comprising the modified protein of the present invention may be found in WO 2006/040129, which is incorporated herein by reference. It is noted that the present invention also encompasses the generation of homo- or heterodimers of the protein of the invention.

According to the present invention, the protein selected for the preparation of the modified protein preferably is human ubiquitin or ubiquitin of another origin, for example another mammalian ubiquitin. Therefore, the invention will be described in the following using particularly human ubiquitin as an example. The modification of human ubiquitin will be described with respect to several examples to obtain a protein which also can be referred to as mutein and which shows a binding affinity with respect to a predetermined binding partner that did not exist previously. As the mammalian ubiquitins there can be particularly used ubiquitins of rodents, domestic animals and agricultural animals among the field of mammals. If the field of use of the proteins prepared according to the invention is known, i.e. if the modified protein shall be for example used as a pharmaceutical composition for the treatment of diseases in humans a human protein can be preferably used as starting protein to be modified; this applies to corresponding fields of use as well. It shall be pointed out that the explanations given below are based on human ubiquitin only by way of example. On the basis of this detailed specification and the examples mentioned it will be possible for those skilled in the art to modify further proteins having ubiquitin-specific folding motifs according to the invention. Thus, the invention is not limited to human ubiquitin or to ubiquitin in general. Indications and explanations in this respect shall be considered as exemplary embodiments of the invention which, however, are particularly preferred.

The following is a short summary regarding the selection and modification of the amino acids to be modified:

On the basis of corresponding structural data such as for example those freely available in PROTEIN DATA BANK™ (Berman et al., 2000; see also the website of the RCSB on the World Wide Web) the positions of those amino acids in the starting protein, e.g. in the ubiquitin protein scaffold, whose side chains are surface-exposed, i.e. directed towards the solvent or a potential binding partner, can be localized by means of computerized analysis (Fraternali and Cavallo 2002). Furthermore, those amino acids in the starting protein, e.g. in ubiquitin, whose random substitution presumably would have no or only a slightly negative effect on the stability of the protein scaffold could be identified by computerized analysis. This information can provide a first indication as to the suitability of every single amino acid as an element of a binding site and would then require further experimental verification. By means of random amino acid substitutions ("randomization") in the region analyzed there can thus be generated—in a manner analogous to the antigen binding site of antibodies—a hypervariable surface-exposed region on the otherwise intact protein structure of ubiquitin.

According to a preferred embodiment—starting from the available structural data of human ubiquitin (PDB 1UBQ)—10 amino acid positions in the region of the binding site to be generated were selected first. By means of site specific random mutagenesis of the primary sequence and subsequent specific selection those variations were obtained which showed the desired binding activity with respect to a predetermined binding partner. Although a de novo binding property is conferred to the modified proteins obtained in this manner they remain to a high degree identical in structure and proteinchemical properties to the starting protein. They provide advantages such as e.g. small size, high stability, cost-effective preparation as well as easy modification together with high affinity and specificity for a previously defined ligand. In this respect, the suitability of ubiquitin as a scaffold structure for the generation of artificial binding proteins could not be expected since 1) the tolerance of the scaffold to the extensive amino acid substitutions could not be expected because of the small size of ubiquitin and 2) the functionality of the artificial binding site involving the helix core structure which is considered as rigid and inflexible did not seem possible beforehand.

According to the invention, antigen shall refer to a substance bound by an antibody. The term antigen comprises haptens, peptides, proteins, sugars, DNA etc. From the Roche Lexikon Medizin (4th edition) the following definition of antigen and hapten can be obtained which is also used for the present invention:

Antigen (AG):

Designation for any substance recognized as foreign ("not self") by the immune system. Initiates in most case an immune reaction leading to immunity (="immunogen"); in the case of allergy (="allergen") and atopy ("atopigen"), respectively, this immune reaction is exaggerated. The AG induces a humoral (antigen-antibody reaction) and/or cellular defence reaction (see below immunity). If the AG is tolerated by the immune system (immune tolerance) it is also referred to as a "tolerogen". Effective as an antigen are mainly complex and higher molecular weight substances (protein bodies, polysaccharides, nucleotides and many synthetic compounds) having chemically identifiable functionalities (determinant) responsible for the immune response. Classified as 1) complete AG, mostly of higher molecular weight and able to arise an immune reaction by itself, 2) as a low molecular weight hapten (=half antigen) which acts as an immunogen only after it is coupled to a larger carrier molecule. Referred to e.g. as xeno-, allo-, or isogenic, autologous AG; auto-, hetero-, transplantation, anti-tumor virus AG.

Hapten:

simple, low molecular weight chemical compound responsible for the specificity of an antigen (AG) or capable of specific binding of the antibody due to its structure (determinant), respectively, but unable to generate an allergy in contrast to a complete AG. Becomes a complete antigen (antigen) after binding to a protein body called carrier.

It shall be pointed out that using the present invention it is also possible to generate variations of ubiquitin which have a binding property with respect to non-immunogenic substances as binding partners, such as e.g. tumor markers.

In a preferred embodiment of the present invention a modification, preferably a substitution, is carried out at least partially at two or more amino acids directly adjacent in the primary sequence wherein the amino acids directly adjacent to each other in the tertiary structure furthermore preferably are localized at least partially in the helix of the protein. In general, every substitution of an amino acid in a protein is accompanied by a potential decrease of the stability of the protein. Single substitutions can mostly be tolerated due to the influence of adjacent amino acids without extensive destabilizations. However, if a whole region, i.e. for example a structural entity consisting of several adjacent amino acids, is changed a stabilizing effect due to the directly adjacent amino acids can no longer be expected.

Particularly in the case of the relatively small ubiquitin the modification of directly adjacent amino acids furthermore has the advantage that it is easier to prepare a modification of this type by genetic engineering than in the case of amino acids which are not directly adjacent to each other. Thus, according to this embodiment the simplified generation of a large number of modified proteins can be provided both on the protein and on the DNA level.

Preferably, the number of substitutions of directly adjacent amino acids is 2 to 10, more preferably 2 to 8 amino acids directly adjacent to each other in the primary sequence, further preferably 3 to 7 or 4 to 6 or 2 to 4 amino acids directly adjacent to each other in the primary sequence.

In a further preferred embodiment 5 or more directly adjacent amino acids are modified, preferably substituted, wherein two or more, preferably two or three, directly adjacent amino acids form the beginning or the end of an alpha helix region. In this case, preferably 8, 9 or 10 amino acids, particularly preferably 8 amino acids can be regarded as an upper limit for the total number of directly adjacent modified amino acids.

In a preferred embodiment of the present invention those amino acids are modified for the generation of a region having the novel binding properties which form a contiguous region on the surface of the protein. In this manner, a contiguous region can be generated which has a binding property that did not exist previously. "Contiguous region" according to the invention refers to the following: due to the charge, the spatial structure and the hydrophobicity/hydrophilicity of their side chains amino acids interact with their environment in the corresponding manner. The environment can be the solvent, generally water, or other molecules, e.g. spatially close amino acids. By means of the structural information about the protein as well as the respective software the surface of the proteins can be characterized. For example, the interface region between the atoms of the protein and the solvent can be visualized in this way including the information about how this interface region is structured, which surface areas are accessible to the solvent or how the charges are distributed on the surface. A contiguous region can be revealed for example by visualization of this type using a suitable software. Such methods are known to those skilled in the art. According to the invention, basically also the whole surface-exposed region can be used as the contiguous region on the surface to be modified for the generation of novel binding properties.

For the mutagenesis of the alpha helix structure preferably those regions are selected in the protein which are close to the surface. Surface-exposed amino acids can be identified with respect to the available x-ray crystallographic structure (Vijay-Kumar, Bugg et al. 1987). If no crystal structure is available attempts can be made by means of computer analysis to predict surface-exposed beta sheet regions and the accessibility of individual amino acid positions with respect to the available primary structure (see e.g. the website of PredictProtein.org) or to model the 3d protein structure (see e.g. the SWISS-MODEL Repository on the website of Expasy.org) and to obtain information about potential surface-exposed amino acids in this manner.

It is also possible, however, to carry out mutageneses in the alpha helix for which the time-consuming pre-selection of amino acid positions to be mutagenized can be omitted. Those DNA regions encoding the alpha helical structures are isolated from their DNA environment, subjected to random mutagenesis and are afterwards re-integrated into the DNA coding for the protein from which they were removed previously. This is followed by a selection process for mutants with the desired binding properties.

Variations of ubiquitin protein scaffold differing by amino acid substitutions in the region of the de novo generated artificial binding site from the parental protein and from each other can be generated by a targeted mutagenesis of the respective sequence segments. In this case, amino acids having certain properties such as polarity, charge, solubility, hydrophobicity or hydrophilicity can be replaced or substituted, respectively, by amino acids with respective other properties. Besides substitutions, the term "mutagenesis" comprises also insertions and deletions. On the protein level the modifications can also be carried out by chemical alteration of the amino acid side chains according to methods known to those skilled in the art.

As a starting point for the mutagenesis of the respective sequence segments for example the cDNA of an ubiquitin-like protein can serve, which can be prepared, altered, and amplified by methods known to those skilled in the art. For site-specific alteration of ubiquitin in relatively small regions of the primary sequence (about 1-3 amino acids) commercially available reagents and methods are on hand (QUICKCHANGE®, Stratagene; "Mutagene Phagemid in vitro Mutagenesis Kit", Biorad). For the site-directed mutagenesis of larger regions specific embodiments of e.g. the polymerase chain reaction (PCR) are available to those skilled in the art. For this purpose a mixture of synthetic oligodeoxynucleotides having degenerated base pair compositions at the desired positions can be used for example for the introduction of the mutation. This can also be achieved by using base pair analogs which do not naturally occur in genomic DNA, such as e.g. inosine.

Starting point for the mutagenesis of the alpha helical region can be for example the cDNA of an ubiquitin-like protein or also the genomic DNA. Furthermore, the gene coding for the protein can also be prepared synthetically.

Different methods known per se are available for mutagenesis which are methods for site-specific mutagenesis, methods for random mutagenesis, mutagenesis using PCR or comparable methods.

In a preferred embodiment of the invention the amino acid positions to be mutagenized are predetermined. The selection of amino acids to be modified is carried out either depending on the protein to be modified and/or depending on the selected binding partner. In each case, a library of different mutants is generally established which is screened using methods known per se. Naturally, a pre-selection of the amino acids to be modified can be particularly easily performed if sufficient structural information is available for the protein to be modified. However, also without such structural information using methods employing random mutagenesis and subsequent selection it is possible to change the protein having the ubiquitin-like folding motif to adopt a binding affinity to the predetermined antigen or binding partner, respectively.

Libraries based on, for example 8, 10, 14 or 18 amino acid positions may be generated (see chapter Example). Preferred library coordinates are: E16, E18, S20, D21, T22, E24, N25, A28, K29, Q31, D32, K33, P38, D39, D52, G53, R54, T55.

Methods for the targeted mutagenesis as well as mutagenesis of longer sequence segments, for example by means of PCR, by chemical mutagenesis or using bacterial mutator strains also belong to the prior art and can be used according to the invention.

In one embodiment of the invention the mutagenesis is carried out by assembly of DNA oligonucleotides carrying the codon triplett stochiometry NNK. It should be understood, however, that also other codon stochiometries can be used, preferably NNB and NWB motives.

In a further embodiment of the invention codon triplett stochiometries, encoding at least 2 or 3 amino acids, preferably 4, 5, 6, 7, 8, 10, 12, 13, 14, 15, 16, 17, 18 or 19 amino acids are used.

The mutations are performed in a way that the secondary structure is maintained. Site-specific mutageneses comprising a relatively small region in the primary structure (about 3-5 amino acids) can be generated with the commercially available kits of Stratagene (QUICKCHANGE®) or Bio-Rad (Mutagene phagemid in vitro mutagenesis kit) (cf. U.S. Pat. No. 5,789,166; U.S. Pat. No. 4,873,192).

If more extended regions are subjected to site-specific mutagenesis a DNA cassette must be prepared wherein the region to be mutagenized is obtained by the assembly of oligonucleotides containing the mutated and the unchanged positions (Nord et al., 1997; McConell and Hoess, 1995). Random mutageneses can be introduced by propagation of the DNA in mutator strains or by PCR amplification (error-prone PCR) (e.g. Pannekoek et al., 1993). For this purpose, a polymerase with an increased error rate is used. To enhance the degree of the mutagenesis introduced or to combine different mutations, respectively, the mutations in the PCR fragments can be combined by means of DNA shuffling (Stemmer, 1994). A review of these mutagenesis strategies with respect to enzymes is provided in the review of Kuchner and Arnold (1997). To carry out this random mutagenesis in a selected DNA region also a DNA cassette must be constructed which is used for mutagenesis.

According to a preferred embodiment of the present invention, only amino acid positions are modified for the generation of a novel binding property which do not belong to regions which in unmodified ubiquitin are involved in linkages to natural binding partners of ubiquitin. This ensures that not only already present binding properties of ubiquitin are altered.

The regions for modification can be basically selected as to whether they can be accessible for a possible binding partner and whether the overall structure of the protein will presumably show tolerance to a modification.

In the protein, preferably ubiquitin from mammals, at least 15% of the amino acids present in alpha helical region, preferably at least 20%, further preferably at least 25%, can be modified, preferably substituted, according to the present invention to generate a binding property that did not exist previously. At a maximum preferably about 40% of the amino acids present in the alpha helical region, further preferably at a maximum about 35% and even more preferably about 30% are modified, preferably substituted. According to a preferred embodiment, the modifications comprise a contiguous region of 5 to 10 amino acids, preferably 6 to 8 amino acids wherein preferably 2 to 4 amino acids thereof lie in a surface-exposed region of the alpha helix.

In the protein according to the present invention, amino acids of the alpha helix strand are modified and optionally additionally amino acids in the helix upstream positions or helix downstream positions lying outside the alpha helix are modified. As mentioned above, in a highly preferred embodiment, the amino acids 22-32 of the alpha helix strand are modified and optionally additionally (in mammalian ubiquitin amino acids) the amino acid regions 16-21 (helix upstream positions) or 38-55 (helix downstream positions) lying outside the alpha helix are modified. Preferably, in the protein of the invention, the modified protein is human ubiquitin substituted, deleted, inserted and/or chemically modified, preferably substituted, at 4 or more of positions 16, 18, 20, 21, 22, 24, 25, 28, 29, 31, 32, 33, 38, 39, 52, 53, 54, and/or 55.

In the protein of the present invention, preferably, a portion of the modified amino acids directly adjacent to each other in the primary sequence is in a starting or an end region of the alpha helix region wherein this portion has a length of two or more amino acids, preferably two or three amino acids.

In a further embodiment, the protein of the invention is human ubiquitin or a protein homologous thereto, wherein at least 4 amino acids of the helix in ubiquitin are modified, preferably substituted, so that these modified amino acids comprise the region with binding affinity to the binding partner.

As mentioned above, the present invention in a main aspect is directed to a method for the generation of a protein selected from the group consisting of proteins of the protein superfamily of "ubiquitin-like proteins", proteins having an ubiquitin-like folding motif as well as fragments or fusion proteins thereof each of which having the ubiquitin-like folding motif, wherein the protein due to one or more modifications of amino acids in the alpha helical region shows an improved binding affinity with respect to an agent which binding affinity did not exist or did not exist to that extent in the unmodified protein, with the following steps:

a) selecting an unmodified protein of the superfamily of "ubiquitin-like proteins";
b) providing an agent to which the unmodified protein has low or no binding affinity;
c) selecting amino acids in a surface-exposed region of the protein including the alpha helix region;
d) modifying the selected amino acids preferably by substitution, insertion, deletion and/or chemical modification, wherein at least four surface-exposed amino acids in the alpha helix or adjacent regions are modified;
e) contacting the modified protein with the agent provided in step b);
f) detecting the proteins having a new or enhanced binding affinity with respect to the agent provided in step b), and optionally
g) producing the modified protein in a suitable prokaryotic, eukaryotic, in vitro protein expression system or by chemical synthesis;
h) isolating the proteins after production by a suitable purification method; and further optionally
i) performing a maturation of the modified protein by repeating the steps d-h)

In a preferred embodiment, step d) is performed by chemical synthesis of the modified protein, or alternatively, the modification in step d) is carried out by means of genetic engineering to alter a DNA belonging to the corresponding modified protein.

As mentioned above, in step d) a gene library preferably is established by random mutagenesis or a random substitution of the selected amino acids is carried out.

In step e), the contacting with the predetermined binding partner is preferably carried out by means of a suitable selection method, preferably the phage display, ribosome display, mRNA display, CIS display or cell surface display method, yeast surface display, bacterial surface display, particularly preferably by means of the phage display method.

In step f), the detection of the proteins having a binding affinity to the predetermined binding partner is preferably carried out by one or more of the following methods: ELISA, plasmon surface resonance spectroscopy, resonance profiling, bead technologies, fluorescence spectroscopy, FACS, isothermal titration calorimetry or analytical ultracentrifugation.

In an embodiment, the protein is maturated by methods known per se with respect to its binding affinity, its binding specificity and/or other proteinchemical properties such as stability, solubility, or yield.

Furthermore, the protein of the invention is linked covalently in a site-specific or random-like manner to at least one protein of the same or a different specificity and thus shows bivalent or multivalent or bispecific binding properties, respectively.

The present invention further provides a protein obtainable by the methods as disclosed hereinabove.

The present invention is further directed to a nucleic acid coding for this protein. Generally, the term "nucleic acid" as used herein encompasses both RNA and DNA, including cDNA, genomic DNA, and synthetic (e.g., chemically synthesized) DNA.

The step of modification of the selected amino acids is performed according to the invention preferably by mutagenesis on the genetic level by random mutagenesis, i.e. a random substitution of the selected amino acids. Preferably, the modification in step d) is carried out by means of methods of genetic engineering for the alteration of a DNA belonging to the respective protein. Preferably, the expression of the protein is then carried out in prokaryotic or eukaryotic organisms.

According to the invention, a modified protein can further preferably be prepared by chemical synthesis. In this embodiment the steps c) to d) of the second embodiment are then performed in one step.

The following illustrates the selection and determination, respectively, of the amino acids with binding affinity with respect to a predetermined binding partner, also simply called "agent" herein:

After a protein library has been established by modification of selected amino acids the modified proteins are contacted according to the invention with a predetermined binding partner to optionally enable binding of the partners to each other if a binding affinity does exist.

Contacting according to the invention is preferably performed by means of a suitable presentation and selection method such as the phage display, ribosome display, mRNA display or cell surface display, yeast surface display or bacterial surface display methods, preferably by means of the phage display method. For complete disclosure, reference is made also to the following references: Hoess, Curr. Opin. Struct. Biol. 3 (1993), 572-579; Wells and Lowmann, Curr. Opin. Struct. Biol. 2 (1992), 597-604; Kay et al., Phage Display of Peptides and Proteins—A Laboratory Manual (1996), Academic Press. The methods mentioned above are known to those skilled in the art and can be used according to the invention including modifications thereof.

The determination whether the modified protein has a quantifiable binding affinity with respect to a predetermined binding partner can be performed according to the invention preferably by one or more of the following methods: ELISA, plasmon surface resonance spectroscopy, fluorescence spectroscopy, FACS, isothermal titration calorimetry and analytical ultracentrifugation.

A type of the phage display procedure adapted to this application is described in the following as an example for a selection procedure according to the invention with respect to variations of ubiquitin which show binding properties. In the same manner e.g. methods for the presentation on bacteria (bacterial surface display; Daugherty et al., 1998) or yeast cells (yeast surface display; Kieke et al., 1997) or cell-free selection systems such as the ribosome display (Hanes and Plückthun, 1997; He and Taussig, 1997) or the cis display (Odegrip et al., 2003) or the mRNA display can be applied. In the latter case a transient physical linkage of genotype and phenotype is achieved by coupling of the protein variation to the appropriate mRNA via the ribosome.

In the phage display procedure described herein recombinant variations of ubiquitin are presented on filamentous phage while the coding DNA of the presented variation is present at the same time packed in a single-stranded form in the phage envelope. Thus, in the frame of an affinity enrichment variations having certain properties can be selected from a library and their genetic information can be amplified by infection of suitable bacteria or added to another cycle of enrichment, respectively. Presentation of the mutated ubiquitin on the phage surface is achieved by genetic fusion to an aminoterminal signal sequence—preferably the PelB signal sequence—and a capsid or surface protein of the phage—preferred is the carboxyterminal fusion to the capsid protein pIII or a fragment thereof. Furthermore, the encoded fusion protein can contain further functional elements such as e.g. an affinity tag or an antibody epitope for detection and/or purification by affinity chromatography or a protease recognition sequence for specific cleavage of the fusion protein in the course of the affinity enrichment. Furthermore, an amber stop codon can be present for example between the gene for the ubiquitin variation and the coding region of the phage capsid protein or the fragment thereof which is not recognized during translation in a suitable suppressor strain partially due to the introduction of one amino acid.

The bacterial vector suitable for the selection procedure in the context of the isolation of ubiquitin variations with binding properties to a predetermined hapten or antigen and into which the gene cassette for the fusion protein described is inserted is referred to as phasmid. Among others, it contains the intergenic region of a filamentous phage (e.g. M13 or f1) or a portion thereof which in the case of a superinfection of the bacterial cell carrying the phagemid by means of helper phages such as e.g. M13K07 results in the packaging of a closed strand of phasmid DNA into a phage capsid. The phagemids generated in this manner are secreted by the bacterium and present the respective ubiquitin variation encoded—due to its fusion to the capsid protein pIII or the fragment thereof-on their surface. Native pIII capsid proteins are present in the phagemid so that its ability to re-infect suitable bacterial strains and therefore the possibility to amplify the corresponding DNA is retained. Thus, the physical linkage between the phenotype of the ubiquitin variation—i.e. its potential binding property—and its genotype is ensured.

Phasmids obtained can be selected with respect to the binding of the ubiquitin variation presented thereon to predetermined haptens or antigens by means of methods known to those skilled in the art. For this purpose, the presented ubiquitin variations can be transiently immobilized to target substance bound e.g. on microtiter plates and can be specifically eluted after non-binding variations have been separated. The elution is preferably performed by basic solutions such as e.g. 100 mM triethylamine. Alternatively, the elution can be performed under acidic conditions, by proteolysis or direct addition of infected bacteria. The phagemids obtained in this manner can be re-amplified and enriched by successive cycles of selection and amplification of ubiquitin variations with binding properties to a predetermined hapten or antigen.

Further characterization of the ubiquitin variations obtained in this way can be performed in the form of the phagemid, i.e. fused to the phage, or after cloning of the corresponding gene cassette into a suitable expression vector in the form of a soluble protein. The appropriate methods are known to those skilled in the art or described in the literature. The characterization can comprise e.g. the determination of the DNA sequence and thus of the primary sequence of the variations isolated. Furthermore, the affinity and specificity of the variations isolated can be detected e.g. by means of immunological standard methods such as ELISA or plasmon surface resonance spectroscopy, fluorescence spectroscopy, FACS, isothermal titration calorimetry or analytical ultracentrifugation. In view of the stability analysis, for example spectroscopic methods in connection with chemical or physical unfolding are known to those skilled in the art.

In the also used ribosome display procedure variations of ubiquitin are prepared by means of a cell-free transcription/translation system and presented as a complex with the corresponding mRNA as well as the ribosome. For this purpose, a DNA library as described above is used as a basis in which the genes of variations are present in form of fusions with the corresponding regulatory sequences for expression and protein biosynthesis. Due to the deletion of the stop codon at the 3' end of the gene library as well as suitable experimental conditions (low temperature, high $Mg^{2+}$ concentration) the ternary complex consisting of the nascent protein, the mRNA and the ribosome is maintained during in vitro transcription/translation.

These complexes can be selected with respect to the binding of the ubiquitin variation presented thereon to predetermined haptens or antigens by means of methods known to those skilled in the art. For this purpose, the ubiquitin variations presented on the ribosomal complexes can be transiently immobilized to target substance bound e.g. on microtiter plates or can be bound to magnetic particles after binding in solution, respectively. Following separation of non-binding variations the genetic information of variations with binding activity can be specifically eluted in the form of the mRNA by destruction of the ribosomal complex. The elution is preferably carried out with 50 mM EDTA. The mRNA obtained in this manner can be isolated and reverse transcribed into DNA using suitable methods (reverse transcriptase reaction), and the DNA obtained in this manner can be re-amplified.

By means of successive cycles of in vitro transcription/translation, selection, and amplification ubiquitin variations with binding properties for a predetermined hapten or antigen can be enriched.

The further characterization of the ubiquitin variations obtained in this manner can be performed in the form of a soluble protein as detailed above after cloning of the corresponding gene cassette into a suitable expression vector. The appropriate methods are known to those skilled in the art or described in the literature.

Following the expression of the proteins modified according to the invention having the ubiquitin-like folding motif these can be further purified and enriched by methods known per se. The selected methods depend on several factors known per se to those skilled in the art, for example the expression vector used, the host organism, the intended field of use, the size of the protein and other factors. For simplified purification the proteins modified according to the invention can be fused to other peptide sequences having an increased affinity to separation materials. Preferably, such fusions are selected that do not have a detrimental effect on the functionality of the ubiquitin protein or can be separated after the purification due to the introduction of specific protease cleavage sites. Such methods are also known per se to those skilled in the art.

According to the invention and particularly according to the procedure described immediately above variations of ubiquitin with a binding affinity with respect to a predetermined binding partner such as e.g. a hapten or antigen can be isolated in general. It is noted that the term "predetermined binding partner" corresponds to the term "agent". As such, "a predetermined binding partner to which a binding affinity did not exist or did not exist to that extent" corresponds to "an agent to which the unmodified protein has a low or no binding affinity".

As the binding partner (agent) for the modified proteins provided according to the invention all biologically and medically active and relevant molecules can be employed. Possible binding partners will be described in the following by way of example. It should be noted, however, that a plurality of other possible ligands can be added to this list. Similar to the relationship between antibody and antigen the list of potential binding partners can be completed by further potential ligands.

Preferably, the binding partner is a biological receptor, preferably a G protein-coupled receptor (GPCR; e.g. human GLP-1 receptor, human PTH receptor, human adrenergic receptor), or EGF receptor, IGF1R, HER2, HER3, VEGF/R1-4, Ep-CAM, or a ligand or a domain thereof, a tumor marker (prostate specific membrane antigen (PSMA)), cytokines (tumor necrosis factor alpha (TNF-$\alpha$), tumor necrosis factor beta (TNF-$\beta$), interleukins (e.g. IL-2, IL-6, IL-8, IL-11, IL-12, IL-13), growth factors (e.g. NGF (nerve growth factor) and the pro-form thereof, ProNGF, BMPs, EGF, MIA, MIA-2, FGFs, vascular endothelial growth factor (VEGF), PDGF, PlGF, IGFs), kinases, integrines (e.g. glycoprotein receptor IIb/IIIa (GPIIb/IIIa)), HSA (human serum albumine), F4 fimbrine, T and B cell antigen, preferably CD4, CD11, CD14, CD16, CD20, CD22, CD25, CD34, CD47, CD56, CD83, CD154, CTLA-4, an immunoglobulin or a portion thereof, for example a whole antibody, (e.g. immunoglobulin G, E, M), an Fc portion of e.g. human immunoglobulin M or a segment of an antibody in the region of the antigen binding site, or a sugar (Lewis Y, Lewis X), or a toxin, for example mycotoxin, or a hormone, for example hydrocortisone.

The proteins of the present invention can furthermore be used for the detection and for quantitative determination as well as for the separation and isolation of the respective binding partner.

Another application is in the diagnosis and treatment of diseases in which the respective binding partner is involved.

As already mentioned, the present invention also relates to the targeted alteration of individual amino acid positions which are localized out of the de novo generated, artificial binding site. In this manner, e.g. positions occupied by amino acids responsible for its biological function in the natural ubiquitin can be occupied by other amino acids. In this manner an ubiquitin protein scaffold is obtained which with respect to its biological functions such as e.g. with respect to the interaction with enzymes of the ubiquitination cascade is inactive but with respect to its structure and proteinchemical properties is largely identical to the starting protein.

For the proteins modified and selected according to the invention, thus, a broad spectrum of possible applications is available. They can be used not only in the medical-pharmaceutical field but also in the field of analytics, of the nutrient and food stuff industry, of nutrient supplements, of cosmetics, of medical and non-medical diagnostics and analysis etc. Naturally, the field of use depends on the type of binding partner selected.

In the field of human and veterinary medical therapy and prophylaxis pharmaceutically effective medicaments can be prepared by methods known per se. Depending on the galenic preparation these compositions can be administered intravenously, intraperitoneally, intramuscularly, subcutaneously, transdermally, or by other methods of application. The type of pharmaceutical preparation depends on the type of disease to be treated, the severity of the disease, the patient to be treated and other factors known to those skilled in the art of medicine. The administration can either be parentally by injection or infusion, inhalation, systemically, orally, rectally of by other methods conventionally employed.

The compositions are adapted to contain a therapeutically effective dose. The quantity of the dose to be administered depends on the organism to be treated, the type of disease, the age and weight of the patient and further factors known per se.

The compositions can contain auxiliary agents known per se. These include for example stabilizing agents, surface-active agents, salts, buffers, coloring agents etc.

The pharmaceutical composition can be in the form of a liquid preparation, a cream, a lotion for topical application, an aerosol, in the form of powders, granules, tablets, suppositories, or capsules, in the form of an emulsion or a liposomal preparation. The compositions are preferably sterile, non-pyrogenic and isotonic and contain the pharmaceutically conventional and acceptable additives known per se. Additionally, reference is made to the regulations of the U.S. pharmacopoeia.

The following Examples are provided for further illustration of the invention. The invention is particularly demonstrated with respect to the modification of ubiquitin as an example. The invention, however, is not limited thereto, and the following Examples merely show the practicability of the invention on the basis of the above description. For a complete disclosure of the invention reference is made also to the literature cited in the application and in the annex which are incorporated in their entirety into the application by reference.

In the following, the present invention will be described in more detail with respect to Examples and the accompanying Figures wherein the following is illustrated:

FIG. 1 Ribbon diagram of human wild type ubiquitin. (PDB 1D3Z; Pymol, Version 0.98)

FIG. 2: Ribbon diagram of human wild type ubiquitin. (PDB 1D3Z). The amino acids, which assemble the hydrophobic core of the protein are painted as green spheres. (Pymol, Version 0.98).

FIG. 3: Ribbon diagram of human wild type ubiquitin. (PDB 1D3Z) The amino acids T22, E24, N25, A28, K29, Q31, D32 and K33 belong to the helix (red). The helix-upstream positions E16, E18, S20, D21 are painted in green. The helix downstream positions P38, D39, D52, G53, R54, T55 are painted in orange. The dominating part of the library is the helix. (Pymol, Version 0.98)

FIG. 4: Surface presentation of human wild type ubiquitin. (PDB 1D3Z) The amino acids T22, E24, N25, A28, K29, Q31, D32 and K33 belong to the helix (red). The helix-upstream positions E16, E18, S20, D21 are painted in green. The helix downstream positions P38, D39, D52, G53, R54, T55 are painted in orange. The dominating part of the library is the helix. (Pymol, Version 0.98)

FIG. 5: Surface presentation of human wild type ubiquitin. (PDB 1D3Z; Pymol, Version 0.98). The maximum binding site of 1485 Å$^2$ is coloured in red.

FIG. 6: Ribbon diagram of human wild type ubiquitin. (PDB 1D3Z; Pymol, Version 0.98) The amino acid position, which assemble the sheet-based library are coloured in blue.

FIG. 7: Surface presentation of human wild type ubiquitin. (PDB 1D3Z; Pymol, Version 0.98). The amino acids, which assemble the sheet-based library are coloured in blue.

FIG. 8: The ribosome display construct SPA10. Primers are painted as blue arrows. The primers forw.MunRD and R3MunEco were used to generate the restriction sites EcoRI and MunI for the latter restriction ligation of the library fragment and the spacer fragment. The primer RDRT was used for the reverse transcription. The primer pairs F1/RDRT and F1A/RDRT were used for the PCR amplifications during the ribosome display selection procedure. Red crosses mark the primers SPAF2, SPAF3 and SPAR2, which introduce the site directed mutations to generate the library.

FIG. 9: Exemplary hit-ELISA showing variants of the SPA10 library versus TNFα (red) and BSA (blue) as a background.

FIG. 10: Amino Acid Sequence of the TNFα binding Ubiquitin variant 2E11 (SEQ ID NO: 14). 10 substituted amino acid positions are marked in yellow. The position K33 turned into E (red).

FIG. 11: Chromatography profile of the SEC (Superdex 75, 1.6×60, GE Healthcare) during the purification of the ubiquitin variant 2E11. The fraction B5 was used for further binding studies.

FIG. 12: ELISA showing the TNFα concentration-dependant binding characteristics of the SPA14 variant 2E11. Filled circles: Variant 2E11 versus TNFα. Empty circles Variant 2E11 versus BSA. By a non linear sigmoidal curve fitting an apparent affinity was determined of 400 nM (R=0.99). The fit was created with Sigma Plot (Vers. 6.10)

EXAMPLES

In the following, data is presented, which describe how a ubiquitin library was constructed using the helix as a central secondary structure motive. Binding active variants versus TNFα were selected via some embodiments of the ribosome display selection technology. The binders were recombinantly produced as soluble proteins in *E. coli*. Variants showing TNFα binding activity were identified by an ELISA hit-screening procedure. By a concentration dependant ELISA the apparent affinity of one of these "first generation" binders to TNFα were determined at 400 nM.

Library Coordinates of the Ubiquitin Library and Different Embodiments Thereof.

The amino acids T22, E24, N25, A28, K29, Q31, D32 and K33 belong to the alpha helix of human ubiquitin and represent the core-positions of the library (FIG. 3). The helix-upstream positions E16, E18, S20, D21 and the helix downstream positions P38, D39, D52, G53, R54, T55 additionally enlarge the surface accessible area to a maximum of 1485 Å$^2$ (FIG. 4, 5). These surrounding positions belong to the connective turn loops of ubiquitin. The position F45 was mutated into W to increase the extinction coefficient to facilitate spectroscopic analyses (Khorasanizadeh, Peters et al. 1993). Altogether a maximum of 11 residues were randomized. Different embodiments of the helix library were constructed. In a first embodiment, the SPA10 library was generated, in which 10 amino acid positions were randomized on the level of DNA using the NNK codon stochiometry (S20, T22, E24, N25, A28, Q31, P38, G53, R54, T55). The SPA10 library should generate a surface of 750 Å$^2$. In a second approach, 14 positions were randomized (SPA14: S20, D21, T22, E24, N25, A28, K29, Q31, D32, P38 D52, G53, R54, T55) in order to generate an enlarged surface of 1011 Å$^2$. The final approach was the SPA18 library, by which 18 residues were mutagenized to generate a maximal surface of 1485 Å$^2$ (E16, E18, S20, D21, T22, E24, N25, A28, K29, Q31, D32, K33, P38, D39, D52, G53, R54, T55).

In the following an example is described, were TNFα binding ubiquitin variants were selected from the SPA 10 library.

Example 1

PCR-Based Synthesis of the SPA10 Library is Described

In an Overlapping Extension Ligation PCR five oligonucleotides were assembled to synthesize the library DNA fragment (FIG. 8). Three of the synthesis primers, SPAF2, SPAF3 and SPAR2, were synthesized as sequence specific randomized oligonucleotides, which encoded the SPA10 helix library.

The first synthesis-step was performed as follows: 100 μl PCR volume containing 0.2 mM dNTPs (10 mM stock, dNTPmix, ROCHE); 5 units PWO Polymerase (250 units stock, ROCHE);

1 μM Primer SPAF1
5'-GTTTAACTTTAAGAAGGAGATATACATATGCAGATTTTTGTGAAAAC
CC-3';

0.25 ∞M Primer SPAF2
5' CACTCTGGAAGTGGAGCCCNNKGACNNKATCNNKNNKGTGAAGNNKA
AGATCNNKGACAAGGAGGGCATCCCG-3';

0.25 μM Primer SPAF3
5'-CTGGGCGGGTAAACAGCTCGAAGACNNKNNKNNKCTGAGCGATTACA
ACATCCAGAAAGAAAGC-3';

1 μM Primer SPAR1
5'-CGCAGACGCAGCACCAGATGCAGGGTGCTTTCTTTCTGGATGTTGTA
ATCGC-3';

0.25 μM Primer SPAR2
5'-CGAGCTGTTTACCCGCCCAGATCAGACGCTGCTGATCMNNCGGGATG
CCCTCCTTGTC-3';

0.25 μM Primer SPAR3
5'-GGGCTCCACTTCCAGAGTGATGGTCTTGCCGGTCAGGGTTTTCACAA
AAATCTGC-3'.

The PCR profile was as follows: (30 sec 94° C.; 60 sec 55° C.; 40 sec 72° C.)×30.

The PCR product was resolved in a 1.5% ethidiumbromide-stained agarose gel. The target DNA-band was extracted at 250 by from the gel using the Qiagen Gel Extraction Kit according to the manufacturer's instructions. To generate a library size of approximately 10$^{11}$ variants at least 100 ng of the purified PCR product of the first synthesis step were transferred as a template into the next Add-on PCR step. In this synthesis step the library fragment is reamplified by terminal primers which add on regulatory sequences like the RBS gene10 motive (F1 primer) and an EcoRI restriction site for the latter restriction ligation procedure. The PCR assay assembled 100 µl volume containing 0.2 mM dNTPs (10 mM stock, dNTPmix, ROCHE); 5 units PWO Polymerase (250 units stock, ROCHE);

```
1 µM Primer F1
5'-GGAGACCACAACGGTTTCCCTCTAGAAATAATTTTGTTTAACTTTAA
GAAGGAGATATACATATG-3'
and 1 µM Primer R3MunEco
5'-GAATTCACTACCTCCGCCGCCACGCAGACGCAGCACCAGATGC-3'.
```

The PCR profile was: (30 sec 94° C.; 60 sec 65° C.; 40 sec 72° C.)×30.

The PCR product was again resolved in a 1.5% ethidiumbromide-stained agarose gel. The target DNA band at 305 by was isolated from the gel and purified like described above.

100 ng of the PCR product from step 2 were transferred into the final synthesis PCR as a template. The PCR setup was as described above, using the Primers F1A

```
                                    (SEQ ID NO: 9)
5'-CATACGAAATTAATACGACTCACTATAGGGAGACCACAACGGTTTCC
C-3'
``` and R3MunEco at 1 µM each. The forward primer F1A introduces a T7 promoter sequence upstream of the DNA fragment. The PCR profile was: (30 sec 94° C.; 60 sec 60° C.; 40 sec 72° C.)×30.

The PCR product was again isolated from a preparative ethidiumbromide-stained 1.5% agarose gel at 333 bp. The PCR product, which resembles the SPA10 encoding DNA fragment was purified as already described above.

The Ribosome Display spacer was generated as follows. The plasmid pIVEX2.3MCSRD contained the DNA sequence of the ribosome display spacer. The sequence has no naturally occurring cognate sequence. It does not contain any stop codons in order to stall the translating ribosome at the 3'-end of the mRNA. The 315 bp spacer sequence is:

```
5'-GGAGGTAGTCAATTGGCTGGCTCTGGAGCTGGTGCAGGCTCTGGTGC

TGGCGCAGGTTCTGGCGCTGGTGCTGGTTCTGGCACTGGTGCTTCTCCGG

CAGCTGTTCCGGCAGCGGTTCCAGCAGCGGTGCCGGCAGCAGTTCCTGCT

GCGGTGGGCGAAGGAGAAGGAGAAGGCGAGGGAGAGGGCGAAGGATACCC

GTACGACGTACCGGACTACGCCGAAGGTGGTGGTGGCTCCGAGCAGAAGC

TCATCTCCGAAGAAGACCTGGAGGGTGGTGGTGGCTCCACAGACTACAAG

GACGACGACGACAAATCC-3'.
```

The PCR setup contained 0.2 mM dNTPs (10 mM stock, dNTPmix, ROCHE); 5 units PWO Polymerase (250 units stock, ROCHE); 5 ng plasmid DNA pIVEX2.3MCSRD in 100 µl volume. The Primers forw.MunRD

```
                                   (SEQ ID NO: 11)
5'-GGCGGCGGAGGTAGTGAATTCGCTGGCTCTGGAGCTGGT-3'
``` and RDRT were used

```
                                   (SEQ ID NO: 12)
5'-GGATTTGTCGTCGTCGTCCTTGTAGTCTGTGGAGCCACCACC-3'
``` at 1 µM each.

The forward primer forw.MunRD introduced a MunI restriction site for the latter restriction ligation procedure of the ribosome display spacer with the library DNA fragment.

The PCR profile was: (30 sec 94° C.; 60 sec 50° C.; 40 sec 72° C.)×30.

The complete PCR assay was electrophoresed in a preparative 1.5% agarose gel. The gel was stained by EtBr and isolated from the gel at 220 bp. The DNA was purified as already described above.

The helix library was ligated to the Ribosome Display spacer using a restriction ligation procedure. In this synthesis step the library DNA fragment was ligated to the ribosome display spacer DNA fragment to generate a fully functional ribosome display construct.

The reaction contained 10 Units (1 µl) MunI (Cat. No. R0589S, NEB), 10 Units (1 µl) EcoRI (Cat. No.: R0101S, NEB), 5 µl 10× buffer NEB4, 1.25 mM ATP solution (25 mM stock, Fermentas), 2.000 units (2.5 µl) T4 DNA Ligase (NEB conc.) 1 µg of the extracted library fragment and 1 µg of the Display Spacer, each in 19 µl solution. After incubation over night at room temperature the complete assay was electrophoresed in a preparative agarose gel. The reaction product was isolated from the gel at 633 by and was extracted using the Qiagen Gel Extraction Kit according to the manufacturer's instructions. Finally, 50 µl eluate was concentrated five-fold using the Qiagen MinElute kit according to the manufacturer's instructions.

Immobilization of Target Molecule in Streptavidin and Avidin—Coated MTP Plates

One Reaction Volume (RV) of an MTP well was washed three times with Conjugate Buffer Universal (Roche). 0.1 µg biotinylated human TNFα was resolved in 100 µl Conjugate Buffer and was filled in the well of the prepared MTP. The biotinylated ligand was immobilized in the wells of Streptavidin- (ROCHE) or Avidin-coated (PIERCE) MT-plates. The ligand-solution was incubated for 30 min at room temperature in the MT-plate under 500 rpm shaking Further MTP-wells were just coated with 100 µl Blocking Reagent (5% BSA in Conjugate Buffer) omitting the ligand. These wells were later on used for a 10 min preincubation of the ribosome display mixtures to deplete unspecific binding ternary complexes. All wells were washed with 3 RV Blocking Reagent. 300 µl Blocking Reagent were incubated in each well for 1 h at 4° C. and 200 rpm. Before the stopped translation-mixture was applied, the wells were washed with 3 RV ice-cold buffer WB (50 mM Tris. pH 7.5 (4° C.); 50 mM magnesiumacetate; 150 mM NaCl; 33 mM KCl; 0.1% TWEEN® 20; 5% BSA). The plates were stored on ice. During the selection cycles the plates were used alternately to deplete background-binding variants.

Ribosome Display with the SPA10 Library Versus Human TNFα.

100 µl RTS 100 *E. coli* HY mixture (Roche) were assembled according to the manufactures instructions. The mixture was supplied with 40 units (1 μl) RNAsin plus (temperature stable RNAse inhibitor, Promega) and 10 μl of the ribosome display DNA template. Transcription and translation was performed in a clean 1.5 ml reaction tube at 30° C. for 40 min under shaking at 550 rpm.

The reaction was immediately stopped with 500 μl ice-cold buffer SB (50 mM Tris. pH 7.5 (4° C.); 50 mM magnesiumacetate; 150 mM NaCl; 33 mM KCl; 0.1% TWEEN® 20; 5% BSA; 5 μg tRNA (*E. coli*); 4 mM GSSG; 25 μM Chloramphenicol). The mixture was centrifuged at >10.000 g at 2° C. for 10 min.

The supernatant was transferred into a fresh, ice-cooled 1.5 ml reaction tube. 250 μl of the mixture were transferred into an empty preincubation-well of a streptavidin-coated MTP and were incubated at 4° C. for 10 min at 300 rpm. The mixture was then transferred into the selection well, in which the biotinylated human TNFα was immobilized. The mixture was incubated for 30 min at 4° C. and 300 rpm.

To remove background protein and weak binding ternary complexes the wells were washed 5 times with 300 μl ice-cold buffer WB (50 mM Tris. pH 7.5 (4° C.); 50 mM magnesiumacetate; 150 mM NaCl; 33 mM KCl; 0.1% TWEEN® 20; 5% BSA). The elution was performed with 100 μl ice-cold buffer EB (50 mM Tris. pH 7.5 (4° C.); 20 mM EDTA; 150 mM NaCl; 33 mM KCl; 0.1% TWEEN® 20; 5% BSA for 10 min at 4° C. and 750 rpm.

100 μl of the eluate were mixed with 350 μl buffer RLT from the Qiagen RNEASY® Kit. The solution was briefly vortexed. The following mRNA purification was according to the manufacturer's instructions. The mRNA was eluted with 50 μl Rnase-free water. The eluate was reused for a second elution-step.

To avoid contamination with DNA from the translation-step, remaining DNA-template in the eluate was removed using the Ambion DNA-free kit (DNA-Digestion). 50 μl eluate were supplemented with 5.7 μl DNAse I buffer and 1.3 μl DNAse I containing solution. The mixture was incubated at 37° C. for 30 min. 6.5 μl DNAse I inactivating reagent was added. The slurry was incubated in the digestion-assay for 3 min at room temperature followed by 1 min centrifugation at 11.000 g. The supernatant was used in the reverse transcription assay.

For the reverse transcription of the mRNA the Transcriptor Reverse Transcriptase (Roche) was used. The complete reaction volume was 20 μl: 12 μl mRNA eluate; 1 μM primer RTRD (SEQ ID NO: 12)
5'-GGATTTGTCGTCGTCGTCCTTGTAGTCTGTGGAGCCACCACC-3';

4 μl Transcriptor Reaction Buffer 5×, RNAsin plus 0.5 μl (20 units, Promega), 1 mM dNTP-mix. The mixture was carefully spinned down. The reaction tube was placed into a 65° C. pre-equilibrated thermocycler. After 5 min at 65° C. min the reverse transcriptase was added at 10 units (0.5 μl). The mixture was subsequently incubated at 65° C. for 45 min.

The cDNA was subsequently amplified in a 100 μl standard PWO-PCR containing 12 μl of the transcription mixture, 5 units PWO DNA-Polymerase and the primers RTRD and F1. The PCR profile was: (30 sec 94° C., 60 sec 65° C.; 40 sec 72° C.)×25 cycles.

The obtained PCR-product was electrophorezed in an 1.5% agarose gel. The respective target DNA-band was extracted from the ethidiumbromide-stained gel using the Qiagen Gel Extraction Kit MinElute kit. The PCR product was eluted in 10 μl EB buffer (Qiagen).

The PCR-product was reamplified in a 100 μl PCR containing the 10 μl eluate, 5 units PWO DNA-Polymerase (hot start) and the primers F1A and RDRT. PCR profile: (30 sec 94° C.; 60 sec 60° C.; 40 sec 72° C.)×30 cycles. The complete PCR assay was electrophoresed in a preparative 1.5% agarose gel and was stained by ethidiumbromide. The target-band was isolated using the Qiagen Gel Extraction kit according to the manufacturer's instructions. The PCR product was eluted in 50 μl EB buffer. This sample was used for the next ribosome display cycle.

The ribosome display procedure was repeated 6 times. In a further embodiment of the selection in the third, fourth and fifth display cycle all necessary amino acids were supplemented separately at 2 mM each to the RTS 100 HY System with the exception of cysteine. Thus, the variants containing cysteine were depleted during the selection. In further embodiments of the selection procedure the selection was performed as selection in solution and as competition in solution using streptavidin-coated magnetic beads.

The beads were prepared as follows: 20 μl of the bead solution (Invitrogen, M270 DYNABEADS®) were washed five times in 300 μl $NaH_2PO_4$ buffer, pH 8. Afterwards the beads were washed 5 times in 300 μl buffer WB and stored in 20 μl buffer WB at 4° C.

In the fourth display cycle selection in solution was performed. 100 ng of the biotinylated human TNFα were incubated for 1 h at 4° C. in the stopped ribosome display translation mixture. In the fifth cycle competition in solution was practiced. 100 ng of the biotinylated human TNFα were incubated together with 10 μg of non-biotinylated TNFα in the stopped ribosome display translation mixture. In both cycles afterwards 10 μl of the prepared bead solution were pipetted to the mixture and were incubated for 30 min at 4° C. in order to capture the biotinylated TNFα together with the pickaback bound ternary complexes from the mixture. The subsequent process steps remained unchanged. The mRNA was eluted from the ternary complexes by incubation of the beads in buffer EB.

Finally the obtained DNA pool from the fifth round of selection was subcloned into the Vector pET20b(+) via the restriction sites NdeI and XhoI. Therefore 100 ng of the linear template DNA from the first ribosome display PCR cycle of the fifth selection round was amplified in a 100 μl PCR containing 5 units PWO DNA-Polymerase and the primers (SEQ ID NO: 13)
5'-GTTTAACTTTAAGAAGGAGATATACATATGCAGATTTTTGTGAAAACCC-3';
and WubiFlagXhoIrv
5'-CCATTCCACCTCGAGACCTTTATCATCATCATCTTTGTAATCGCCGCCACGCAGACGCAGC.

By using this primer-pair the DNA sequences encoded for ubiquitin variants fused C-terminally with the Flag-epitope and hexahistidine sequence. The PCR profile was: (30 sec 94° C., 60 sec 65° C.; 40 sec 72° C.)×30 cycles. The PCR product was purified using the Qiagen PCR Purification kit according to the manufacturer's instructions. The purified PCR product was restricted in a double digest using the enzymes NdeI and XhoI. The 40 μl digestion reaction contained 500 ng PCR product in 10 μl 10 mM Tris buffer pH 8, 12 units NdeI (Promega); 12 units XhoI (Promega), 4 μl buffer D (Promega), 0.1 mg/ml BSA. The mixture was incubated at 37° C. for 12 h. The digested DNA fragment was purified by a preparative agarose gel like described above. The vector DNA pet20b(+) was digested in a 60 μl reaction. 1 μg of plasmid-DNA in 30 μl 10 mM Tris buffer pH 8 was pipetted to 6 μl buffer D (Promega), 0.1 mg/ml BSA, 24 units NdeI and XhoI each (Promega). The mixture was incubated at 37° C. for 12 h. The digested DNA fragment was purified by a preparative agarose gel like described above. The ligation reaction was performed using the Rapid Ligation Kit (Roche) according to the manufacturer's instructions. The Ligation reaction was purified using the Qiagen Reaction Cleanup kit according to the manufacturer's instructions. The purified ligation product was transformed into *E. coli* electrocompetent cells (NovaBlue, NOVAGEN®).

The transformants were plated on a selective Luria-Bertanii broth agar-plate (Q-Tray) containing ampicillin at 100 μg/ml. The plate was incubated for 12 h at 37° C. Single colonies were separated in 5 MTPs containing 250 μl Luria-Bertanii broth medium containing ampicillin at 60 μg/ml. The MTPs were incubated at 37° C. for 12 h. 1.5 ml Luria-Bertanii broth medium containing ampicillin at 60 μg/ml were inoculated with 60 μl of the preparatory cultures. The remaining culture volumes were stored at −20° C. After 2 h of incubation at 37° C. and vigorous shaking at 700 rpm the recombinant protein production was induced by 0.1 mM IPTG for 4 h at 30° C. The Deep well blocks were centrifuged for 15 min at 3600×g at 4° C. in the Heraeus Multifuge 3 L-R using the rotor 75006445 (Heraeus). The supernatant was removed and the cell pellets were lysed 30 min at room temperature using 300 μl NPI0 buffer (50 mM NaH$_2$PO$_4$, 300 mM NaCl, 1 mg/ml T4 lysozyme, 10 μl/ml BUGBUSTER® (Novagen); 4 mM MgCl$_2$; 0.8 mM PMSF; 20 units/10 ml Benzonase (VWR)).

The cell debris was again centrifuged for 15 min at 3600×g at 4° C. in the Heraeus Multifuge 3 L-R. The supernatant was transferred into a clean MTP.

Hit-Elisa to Identify Ubiquitin Binding Variants

Nunc MEDISORP® ELISA plates were washed three times with 300 μl PBST buffer (PBS pH 7.4; 0.1% TWEEN® 20). TNFα was diluted in PBS buffer at 1 μg/ml. 50 μl of the solution were incubated for 1 h at room temperature in the even-numbered columns of the plates.

BSA was diluted at 10 μg/ml in PBS buffer and was 50 μl PBS. 50 μl of the solution were incubated for 1 h at room temperature in the odd-numbered columns. The plates were washed with 300 μl PBST buffer. The wells were filled with 300 μl Blocking buffer (PBS pH 7.4; 3% BSA; 0.5% TWEEN® 20) and were incubated at room temperature for 4 h. The plates were washed three times with 300 μl PBST buffer. 60 μl of each centrifuged supernatant sample was applied to one even-numbered TNFα coated well and to the neighbouring odd-numbered BSA-coated well and was incubated for 1 h at room temperature. The plates were washed three times with 300 μl buffer PBST. 50 μl of the Anti-Flag-POD conjugate M2 (Sigma) were added to the wells (1:2000 dilution in PBST pH 7.4) and were incubated for 1 h at room temperature. The plate was washed three timers with 300 μl buffer PBST. 50 μl TMB substrate solution (KEM-EN-Tec) were pipetted to the wells and were incubated for 15 min. The reaction was stopped by 50 μl 0.2 M H$_2$SO$_4$. The ELISA plates were read out using the TECAN Sunrise ELISA-Reader. The photometric absorbance measurements were done at 450 nm using 620 nm as a reference (FIG. 9).

Visualization of Expressed Ubiquitin Variants

10 μl of the *E. coli* supernatant were resolved by PAGE electrophoresis. The acrylamide gels were coomassie-stained to analyse the soluble protein portion of the variants.

The clones, which appeared as soluble fraction in the coomassie-stained gel and which showed target molecule binding activity in the hit-ELISA were selected for the DNA sequencing process.

Production and Purification of TNFα Binding Ubiquitin Variant 2E11

In order to study the binding properties of a selected mutant in detail, the ubiquitin variant 2E11 (FIG. 10) was purified. NovaBlue (NOVAGEN®) *E. coli* cells were transformed with plasmids pET 20b+/22E11. The clones were cultivated by diluting a preculture 1:100 with LB medium/100 μg/ml ampicillin and agitating the culture at 200 rpm and 37° C. up to an OD$_{600}$ of 0.5. Expression was induced by adding IPTG (final concentration 1 mM). Culturing was continued overnight at 30° C. and 200 rpm. The bacteria cells were harvested by centrifugation at 4° C., 6000×g for 20 min. The cell pellet was suspended in 30 ml of NPI-20 buffer including DNAse and 10 mg/ml lysozyme. The variant 2E11 was purified with 5 mM CHAPS in all buffer systems. The cells were disrupted twice using a Gaulin press at 800-1000 PSIG. The supernatant containing the soluble proteins was obtained after centrifugation of the cell suspension at 4° C. and 40000×g for 30 min.

One column of Ni-NTA-Agarose (5 ml, GE Healthcare) were equilibrated with 5 CV of NPI-20. The supernatant containing the soluble proteins was applied to the column, followed by washing with 5 CV NPI-20. The bound protein was eluted with a linear gradient to 50% NPI-500 in 20 CV. Fractions were eluted at 2 ml each and were analyzed by SDS-PAGE with respect to their purity. Fractions containing the target protein were pooled and applied to a gelfiltration column (SUPERDEX™ 75, 1.6×60, GE Healthcare) equilibrated with PBS (pH 7.4) at a flow rate of 1 ml/min (FIG. 11). Purified protein was used for binding experiments.

ELISA for Determining Specific Binding

Specific binding of mutant 2E11 to human TNFα was assayed by a concentration dependant ELISA. Increasing amounts of purified AFFILIN® ubiquitin variant 2E11 were applied to Nunc MEDISORP® plates coated with BSA as controls. Antigen coating with 50 μl (1 μg/ml) per well was performed at 4° C. overnight. After washing the plates with PBS, 0.1% TWEEN® 20, pH 7.4 (PBST), the wells were blocked using blocking solution (PBS pH 7.4; 3% BSA; 0.5% TWEEN® 20) at 37° C. for 2 h. Wells were washed again with PBST. Different concentrations of ubiquitin variant 2E11 in 50 μl were then incubated in the wells at 37° C. for 1 h. After washing the wells with PBST the anti-FLAG POD conjugate (Sigma) was applied in a dilution of 1:2000 in PBST. Substrate reaction and signal read out was done as described in the Hit-ELISA chapter. FIG. 12 shows the specific binding of the ubiquitin variant 2E11 to human TNFα with an apparent KD value of 400 nM.

REFERENCES

Ausubel, F. M., Brent, R., Kinston, R. E., Moore, D. D., Seidmann, J. G., Smith, J. A., and Struhl, K. (1994): Current protocols in molecular biology. John Wiley & Sons, Inc.

Bazarsuren, A., Grauschopf, U., Wozny, M., Reusch, D., Hoffmann, E., Schaefer, W., Panzner, S., and Rudolph, R. (2002) In vitro folding, functional characterization, and disulfide pattern of the extracellular domain of human GLP-1 receptor. Biophys. Chem. 96, 305-318.

Beal, R., Deveraux, Q., Xia, G., Rechsteiner, M., and Pickart, C. (1996) Surface hydrophobic residues of multiubiquitin chains essential for proteolytic targeting. Proc. Natl. Acad. Sci. USA 93, 861-866.

Berman, H. M., Westbrook, J., Feng, Z., Gilliland, G., Bhat, T. N., Weissig, H., Shindyalov, I. N., and Bourne, P. E. (2000) The Protein Data Bank. Nucleic Acid Res., 28, 235-242.

Beste, G., Schmidt, F. S., Stibora, T., and Skerra, A. (1999) Small antibody-like proteins with predescribed Ligand specificities derived from the lipocalin fold. Proc. Natl. Acad. Sci. USA 96, 1898-1903.

Bird, R. E., Hardman, K. D., Jacobson, J. W., Johnson, S., Kaufman, R., Lee, S. M., Pope, H. S., Riordan, G. S., and Whitlow, M. (1988) Single-chain antigen-binding proteins. Science 242, 423-426.

Burch, T. J. and Haas, A. L. (1994) Site-directed mutagenesis of Ubiquitin. Differential roles for Arginine in the interaction with Ubiquitin-activating enzyme. Biochemistry 33, 7300-7308.

Brinkmann, U., Reiter, Y., Jung, S. H., Lee, B., and Pastan, I. (1993) A recombinant immunotoxin containing a disulfide-stabilized Fv-fragment. Proc. Natl. Acad. Sci. USA 90, 7538-7542.

Buchberger A, Howard M J, Proctor M, Bycroft M, National Library of Medicine, J Mol. Biol. 2001 Mr 16; 307(1); 17-24.

Calter, P., Kelley, R. F., Rodrigues, M. L., Snedecor, B., Covarrubias, M., Velligan, M. D., Wong, W. L. T., Rowland, Kotts, C. E., Carver, M. E., Yang, M., Bourell, J. H., Shepard, H., Connolly, M. L. (1983) "Solvent-Accessible Surfaces of Proteins and Nucleic Acids" Science, 221, 709-713.

M. and Henner, D. (1992) High level *Escherichia coli* expression and production of a bivalent humanized antibody fragment. Biotechnology 10, 163-167.

Daugherty, P. S., Chen, G., Olsen, M. J., Iverson, B. L., and Georgiou, G. (1998) Antibody affinity maturation using bacterial surface display. Protein Eng. 11, 825-832.

Dübel, S. and Kontermann, R. E. (2001) Recombinant Antibodies. In: Kontermann, R. and Dübel, S. (Hrsg.) "Antibody Engineering." Springer Verlag, Heidelberg.

Filippi, M., Triboli, C., and Toniolo, D. (1990) Linkage and sequence conservation of the X-linked genes DX253 (P3) and DXS254E (GdX) in mouse and man. Genomics 7, 453-457.

Griep, R. A., van Twisk, C., van der Wolf, J. M., and Schots, A. (1999) Fluobodies: green fluorescent single-chain Fv fusion proteins. J. Immunol. Methods 230, 121-130.

Hanes, J., Jermutus, L., Weber-Bornhauser, S., Bosshard, H. R., and Plückthun, A. (1998) Ribosome display efficiently selects and evolves high-affinity antibodies in vitro from immune libraries. Proc. Natl. Acad. Sci. USA 95, 14130-14135.

Hanes, J., Schaffitzel, C., Knappik, A., and Plückthun, A. (2000) Picomolar affinity antibodies from a fully synthetic naive library selected and evolved by ribosome display. Nature Biotechnology 18, 1287-1292.

He, M. and Taussig, M. J. (1997) Antibody-ribosome-mRNA (ARM) complexes as efficient selection particles for in vitro display and evolution of antibody combining sites. Nucleic Acids Res. 25, 5132-5134.

Holliger, P., Prospero, T., and Winter, G. (1993) "Diabodies": small bivalent and bispecific antibodies. Proc. Natl. Sci. USA 90, 6444-6448.

Hoogenboom, H. R., de Bruine, A. P., Hufton, S. E., Hoet, R. M., Arends, J. W., and Roovers, R. C. (1998) Antibody phage display technology and its applications. Immunotechnology 4, 1-20.

Jones, D. and Candido, E. P. (1993) Novel ubiquitin-like ribosome protein fusion genes from the nematodes *Caenorhabditis elegans* and *Caenorhabditis briggsae*. J. Biol. Chem. 268, 19545-195451.

Kieke, M. C., Cho, B. K., Boder, E. T., Kranz, D. M., and Wittrup, K. D. (1997) Isolation of anti-T cell receptor scFv mutants by yeast surface display. Protein Eng. 10, 1303-1310.

Knappik, A., Ge, S., Honegger, A., Pack, P., Fischer, M., Wellnhofer, G., Hoess, A., Wolle, J., Plückthun, A., and Virnekäs, B. (2000) Fully synthetic human combinatorial antibody libraries (HuCAL) based on modular consensus frameworks and CDRs randomized with trinucleotides. J. Mol. Biol., 296, 57-86.

Koide, A., Bailey, C. W., Huang, X., and Koide, S. (1998) The fibronectin type III domain as a scaffold for novel binding proteins. J. Mol. Biol. 284, 1141-1151.

Kuchner, O. and Arnold, F. H. (1997): Directed evolution of enzyme catalysts. TIBTECH 15, 523-530.

Kumar, S., Yoshida, Y., and Noda, M. (1993) Cloning of a cDNA which encodes a novel ubiquitin-like protein. Biochem. Biophys. Res. Comniun. 195, 393-399.

Larsen C N, Wang H., National Library of Medicine; J Proteome Res. 2002 September-October; 1(5): 411-9.

Marx, J. (2002) Ubiquitin lives up to its name. Science 297, 1792-1794.

McConell S. and Hoess R. H. (1995): Tendamistat as a scaffold for conformationally constrained phage peptide libraries. J. Mol. Biol. 250, 460-470.

Michiels, L., Van der Rauwelaert, E., Van Hasselt, F., Kas, K., and Merregaert, J. (1993) Fau cDNA encodes a ubiquitin-like-S30 fusion protein and is expressed as an antisense sequence in the Finkel-Biskis-Reilly murine sarcoma virus. Oncogene 8, 2537-2546.

Miura, T., Klaus, W., Gsell, B., Miyamoto, C., and Senn, H. (1999) Characterization of the binding interface between ubiquitin and class 1 human ubiquitin-conjugating enzyme 2b by multidimensional heteronuclear NMR spectroscopy in solution. J. Mol. Biol. 290, 213-228.

Muller, B. H., Chevrier, D., Boulain, J.-C., and Guesdon, J.-L. (1999) Recombinant single-chain Fv antibody fragment-alkaline phosphatase conjugate for one-step immunodetection in molecular hybridization. J. Immunol. Methods 227, 177-185.

Muller, S., Hoege, C., Pyrowolakis, G., and Jentsch, S. (2001) SUMO, ubiquitin's mysterious cousin. Nat. Rev. Mol. Cell. Biol. 2, 202-210.

Murzin A. G., Brenner S. E., Hubbard T., and Chothia C. (1995). SCOP: a structural classification of proteins database for the investigation of sequences and structures. J. Mol. Biol. 247, 536-540.

Nord, K., Gunneriusson, E., Ringdahl, J., Stahl, S., Uhlen, M., and Nygren, P. A. (1997); Binding proteins selected from combinatorial libraries of an beta-helical bacterial receptor domain. Nat. Biotechnol. 8, 772-777.

Odegrip, R., Coomber, D., Eldridge, B., Herderer, R., Kuhlman, P. A., Ullman, C., FitzGerald, K., and McGregor, D. (2003) CIS display: In vitro selection of peptides from libraries of protein-DNA complexes. PNAS101, 2806-2810.

Pannekoek, H., van Meijer, M., Schleef, R. R., Loskutoff, d. J., and Barbas, C. F. (1993): Functional display of human plasminogen-activator inhibitor 1 (PAI-1) on phages: Novel perspectives for structure-function analysis by error-prone DNA synthesis. Gene 128, 135-140.

Reiter, Y. and Pastan, I. (1998) Recombinant Fv immunotoxins and Fv fragments as novel agents for cancer therapy and diagnosis. Trends Biotechnol. 16, 513-520.

Sambrook, J., Maniatis, T., and Fritsch, E. F. (1989): Molecular Cloning: A laboratory manual. Cold Spring Harbor. Cold Spring Harbor Laboratory Press, New York.

Sambrook, J., Fritsch, E. F., and Maniatis, T. (2001) "Molecular Cloning: A Laboratory Manual" 3rd ed. Cold Spring Harbor Laboratory Press, Cold Spring Harbor, N. Y.

Shrake, A. and Rupley, J. A. (1973) Environment and Exposure to Solvent of Protein Atoms. Lysozyme and Insuline. J. Mol. Biol. 79, 351-371.

Skena, A. and Plückthun, A. (1988) Assembly of a functional immunoglobulin Fv fragment in *Escherichia coli*. Science 240, 1038-1041.

Schaffitzel, C., Zahnd, C., Amstutz, P., Luginbuhl, B., and Plückthun, A. (2001) In vitro selection and evolution of protein-ligand interactions by ribosome display. In: Protein-Protein Interactions, A Molecular Cloning Manual, E. Golemis, Ed. (Cold Spring Harbor Laboratory Press, New York, 2001, pp. 535-567.)

Skerra, A. (2000) Engineered protein scaffolds for molecular recognition. J. Mol. Recognit. 13, 167-187.

Stemmer, W. P. C. (1994): Rapid evolution of a protein in vitro by DNA shuffling. Nature 370, 389-391.

Vijay-Kumar, S., Bugg, C. E., and Cook, W. J. (1987) Structure of ubiquitin refined at 1.8 A resolution. J. Mol. Biol. 194, 531-544.

Winter, G. (1998) Synthetic human antibodies and a strategy for protein engineering. FEBS Lett. 430, 92-94.

Wintrode, P. L., Makhatadze, G. I., and Privalov, P. L. (1994) Thermodynamics of ubiquitin unfolding. Proteins Struct. Funct. Genet. 18, 246-253.

Bofill, R. and M. S. Searle (2005). "Engineering stabilising beta-sheet interactions into a conformationally flexible region of the folding transition state of ubiquitin." *J Mol Biol* 353(2): 373-84.

Crespo, M. D., E. R. Simpson, et al. (2006). "Population of on-pathway intermediates in the folding of ubiquitin." *J Mol Biol* 360(5): 1053-66.

Fraternali, F. and L. Cavallo (2002). "Parameter optimized surfaces (POPS): analysis of key interactions and conformational changes in the ribosome." *Nucleic Acids Res* 30(13): 2950-60.

Jackson, S. E. (2006). "Ubiquitin: a small protein folding paradigm." *Org Biomol Chem* 4(10): 1845-53.

Khorasanizadeh, S., I. D. Peters, et al. (1993). "Folding and stability of a tryptophan-containing mutant of ubiquitin." *Biochemistry* 32(27): 7054-63.

Pandit, A. D., A. Jha, et al. (2006). "Small Proteins Fold Through Transition States With Native-like Topologies." *J Mol Biol* 361(4): 755-70.

Vijay-Kumar, S., C. E. Bugg, et al. (1987). "Comparison of the three-dimensional structures of human, yeast, and oat ubiquitin." *J Biol Chem* 262(13): 6396-9.

What is claimed is:

1. A method for producing a modified mammalian ubiquitin protein having a new or improved binding affinity with respect to an agent, the method comprising:
   a) selecting an unmodified mammalian ubiquitin protein comprising SEQ ID NO: 15;
   b) providing an agent to which the unmodified mammalian ubiquitin protein has low or no binding affinity;
   c) selecting at least four amino acids from among amino acids 16, 18, 20-22, 24, 25, 28, 29, 31-33, 38, 39, and 52-55 of SEQ ID NO: 15;
   d) substituting the selected at least four amino acids to produce a modified mammalian ubiquitin protein, wherein at least each of amino acids 22, 24, 25, and 28 of SEQ ID NO: 15 is substituted;
   e) contacting the modified mammalian ubiquitin protein with the agent provided in step b); and
   f) isolating a modified mammalian ubiquitin protein having a new or improved binding affinity with respect to the agent provided in step b, wherein a modified mammalian ubiquitin protein having a new or improved binding affinity with respect to the agent is produced.

2. The method according to claim 1, wherein step d) is performed by chemical synthesis of the modified mammalian ubiquitin protein.

3. The method according to claim 1, wherein the modification in step d) is carried out by means of genetic engineering to alter a DNA belonging to the corresponding modified protein.

4. The method according to claim 1, wherein in step d) a gene library is established.

5. The method according to claim 1, wherein in step d) by random mutagenesis a random substitution of the selected amino acids is carried out.

6. The method according to claim 1, wherein in step e) the contacting with the agent is carried out by means of a suitable selection method.

7. The method of claim 6, wherein the selection method is selected from the phage display, ribosomal display, mRNA display, CIS display or cell surface display method, yeast surface display, bacterial surface display method.

8. The method according to claim 1, wherein in step f) the detection of the modified mammalian ubiquitin protein having a binding affinity to the agent is carried out by one or more of the following methods: ELISA, plasmon surface resonance spectroscopy, fluorescence spectroscopy, FACS, isothermal titration calorimetry or analytical ultracentrifugation.

9. The method according to claim 1, further comprising maturing the modified mammalian ubiquitin protein by introducing additional modifications into the modified mammalian ubiquitin protein isolated in step f) to improve its binding affinity with respect to the agent, its binding specificity with respect to the agent, and/or another protein chemical property selected from the group consisting of stability, solubility, and yield.

10. The method according to claim 1, wherein the modified mammalian protein is linked covalently in a site-specific or random manner to at least one protein of the same or a different specificity, whereby a bivalent, multivalent, or bispecific binding protein is obtained.

11. The method according to claim 1, wherein the unmodified mammalian ubiquitin protein is a human ubiquitin.

12. The method according to claim 1, further comprising substituting at least one of amino acids 29, 31 and 32 of SEQ ID NO: 15.

13. The method of claim 1, wherein the substituted amino acids from in the secondary structure of the modified mammalian ubiquitin protein a contiguous binding region for the agent.

14. The method of claim 1, further comprising substituting additional adjacent amino acids in SEQ ID NO: 15.

15. The method according to claim 1, wherein the substituting step comprises substituting amino acids that in the unmodified mammalian ubiquitin protein do not participate in binding to natural binding partners of ubiquitin.

16. The method according to claim 1, further comprising substituting six of amino acids 16, 18, 20-21, 29, 31-33, 38, 39 and 52-55 of SEQ ID NO 15.

17. The method according to claim 1, further comprising substituting four of amino acids 16, 18, 20-21, 29, 31-33, 38, 39 and 52-55 of SEQ ID NO 15.

18. The method according to claim 1, wherein the agent is an antigen or a hapten.

19. The method according to claim 1, wherein the binding affinity, expressed in KD, of the modified mammalian ubiquitin protein to the agent is $10^{-5}$ M to $10^{-12}$ M.

20. The method according to claim 19, wherein the binding affinity, expressed in KD, of the modified mammalian ubiquitin protein to the agent is $10^{-6}$ to $10^{-12}$ M or $10^{-9}$ to $10^{-12}$ M.

21. The method according to claim 1, wherein the modified mammalian ubiquitin protein is linked covalently in a site-specific or random-like manner to at least one protein of the same or a different specificity to create a bivalent, multivalent, or bispecific binding protein.

22. The method of claim 1, further comprising:
g) producing the modified mammalian ubiquitin protein in a suitable prokaryotic, eukaryotic, or in vitro expression system, or by chemical synthesis; and
h) isolating the modified mammalian ubiquitin protein.

23. The method of claim 22, further comprising i) maturing the modified mammalian ubiquitin protein by repeating the steps d-h) to improve one or more of the modified mammalian ubiquitin protein's binding affinity with respect to the agent, binding specificity with respect to the agent, stability, solubility, and yield.

24. The method according to claim 12, further comprising substituting at least one additional amino acid selected from among amino acids 16-21 and 38-55 of SEQ ID NO: 15.

25. The method of claim 1, wherein the modified mammalian ubiquitin protein further comprises at least one additional substitution from among amino acids 16, 18, 20, 21 and 29, 31-33, 38, 39, and 52-55 of SEQ ID NO: 15.

26. The method of claim 1, wherein the modified mammalian ubiquitin further comprises one or more additional substitutions selected from the group consisting of:
(i) each of amino acids 31 and 32 of SEQ ID NO: 15;
(ii) each of amino acids 21, 31, 32, and 38 of SEQ ID NO: 15;
(iii) each of amino acids 20, 21, 29, 31, 32, and 38 of SEQ ID NO: 15;
(iv) each of amino acids 20, 21, 29, 31, 32, 38, 52, and 53 of SEQ ID NO: 15;
(v) each of amino acids 20, 21, 29, 31, 32, 38, and 52-55 of SEQ ID NO: 15;
(vi) each of amino acids 16, 18, 20, 21, 29, 31, 32, 38, and 52-55 of SEQ ID NO: 15; and
(vii) each of amino acids 16, 18, 20, 21, 29, 31-33, 38, 39, and 52-55 of SEQ ID NO: 15.

27. The method of claim 1, wherein the agent is human tumor necrosis factor-α (TNFα).

28. The method of claim 9, wherein the additional modifications comprise one or more substitutions, insertions, deletions, chemical modifications, or any combination thereof.

* * * * *